(12) United States Patent
Chen et al.

(10) Patent No.: US 11,630,102 B2
(45) Date of Patent: Apr. 18, 2023

(54) COMPOSITION AND METHOD FOR MODULATING FIBROBLAST GROWTH FACTOR RECEPTOR 3 ACTIVATION

(71) Applicant: ACADEMIA SINICA, Taipei (TW)

(72) Inventors: Yuan-Tsong Chen, Luzhu Township (TW); Yi-Ching Lee, New Taipei (TW); Jer-Yuam Wu, New Taipei (TW); Hsiao-Jung Kao, Taipei (TW)

(73) Assignee: ACADEMIA SINICA, Taipei (TW)

( * ) Notice: Subject to any disclaimer, the term of this patent is extended or adjusted under 35 U.S.C. 154(b) by 519 days.

(21) Appl. No.: 16/484,948

(22) PCT Filed: Feb. 8, 2018

(86) PCT No.: PCT/US2018/017376
§ 371 (c)(1),
(2) Date: Aug. 9, 2019

(87) PCT Pub. No.: WO2018/148376
PCT Pub. Date: Aug. 16, 2018

(65) Prior Publication Data
US 2019/0361004 A1    Nov. 28, 2019

Related U.S. Application Data

(60) Provisional application No. 62/457,423, filed on Feb. 10, 2017.

(51) Int. Cl.
| | | |
|---|---|---|
| *A01K 67/027* | (2006.01) | |
| *G01N 33/50* | (2006.01) | |
| *A61P 19/00* | (2006.01) | |
| *A61P 35/00* | (2006.01) | |
| *A61K 31/409* | (2006.01) | |
| *A61K 36/21* | (2006.01) | |

(52) U.S. Cl.
CPC ....... *G01N 33/502* (2013.01); *A01K 67/0278* (2013.01); *A61K 31/409* (2013.01); *A61K 36/21* (2013.01); *A61P 19/00* (2018.01); *A61P 35/00* (2018.01); *A01K 2217/072* (2013.01); *A01K 2227/105* (2013.01); *A01K 2267/0331* (2013.01); *G01N 2500/10* (2013.01)

(58) Field of Classification Search
None
See application file for complete search history.

(56) References Cited

U.S. PATENT DOCUMENTS

| | | | |
|---|---|---|---|
| 6,265,632 B1 * | 7/2001 | Yayon | C07K 14/71 800/9 |
| 6,689,610 B1 * | 2/2004 | Capecchi | C07K 14/47 435/463 |
| 2008/0254040 A1 | 10/2008 | Stefanic et al. | |

OTHER PUBLICATIONS

Liu et al., 2003 Genome Res 13, 476-484 A Highly Efficient Recombineering-Based Method for Generating Conditional Knockout Mutations.*
Capecchi et al. 2005; Gene targeting in mice: functional analysis of the mammalian genome for the twenty-first century pp. 507-512.*
Monsonego-Ornan, E., Adar, R., Feferman, T., Segev, O. & Yayon, A. (2000) Mol. Cell. Biol. 20, 516-522.*
Segev et al. Restrained chondrocyte proliferation and maturation with abnormal growth plate vascularization and ossification in human FGFR-3G380R transgenic mice Human Molecular Genetics, 2000, vol. 9, No. 2 249-258.*
Perez-Castro et a l., Genomic Organization of the Human Fibroblast Growth Factor Receptor 3 (FGFR3) Gene and Comparative Sequence Analysis with the Mouse Fgfr3 Gene GENOMICS 41, 10-16 (1997).*
Chen et al., "Adapter Protein SH2-Bβ Undergoes Nucleocytoplasmic Shuttling: Implications for Nerve Growth Factor Induction of Neuronal Differentiation," Molecular and Cellular Biology, May 2004, vol. 24, No. 9, pp. 3633-3647.
Cho et al., "Defective lysosomal targeting of activated fibroblast growth factor receptor 3 in achondroplasia," PNAS, Jan. 13, 2004, vol. 101, No. 2, pp. 609-614.
Fernández-Arroyo et al., "The impact of polyphenols on chondrocyte growth and survival: a preliminary report," Food & Nutrition Research, Oct. 5, 2015, vol. 59, Article No. 29311, pp. 1-10.
International Search Report (PCT/ISA/210) issued in PCT/US2018/017376, dated May 31, 2018.
Lee et al., "Knock-in human FGFR3 achondroplasia mutation as a mouse model for human skeletal dysplasia," Scientific Reports, Feb. 23, 2017, vol. 7, Article No. 43220, pp. 1-10.
Monsonego-Ornan et al., "The Transmembrane Mutation G380R in Fibroblast Growth Factor Receptor 3 Uncouples Ligand-Mediated Receptor Activation from Down-Regulation," Molecular and Cellular Biology, Jan. 2000, vol. 20, No. 2, pp. 516-522.
Written Opinion of the International Searching Authority (PCT/ISA/237) issued in PCT/US2018/017376, dated May 31, 2018.

\* cited by examiner

*Primary Examiner* — Maria G Leavitt
(74) *Attorney, Agent, or Firm* — Birch, Stewart, Kolasch & Birch, LLP

(57) ABSTRACT

A method of inhibiting an overactive fibroblast growth factor receptor 3 (FGFR3) in a cell by contacting the cell with a composition that contains an effective amount of Pheophorbide a, Pyropheophorbide a, or an active derivative thereof. Also disclosed is a method for treating a disorder associated with an overactive FGFR3 with a composition containing an effective amount of Pheophorbide a, Pyropheophorbide a, or an active derivative thereof. Further, a composition for treating a disorder associated with an overactive FGFR3 is described. The composition contains an ethanol extract of *Amaranthus viridis*.

4 Claims, 10 Drawing Sheets
Specification includes a Sequence Listing.

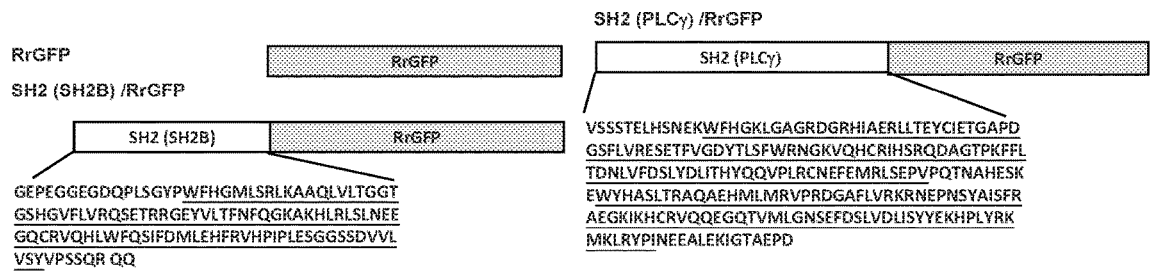
Fig. 5A
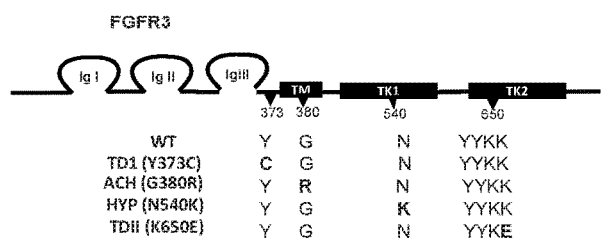
Fig. 5B
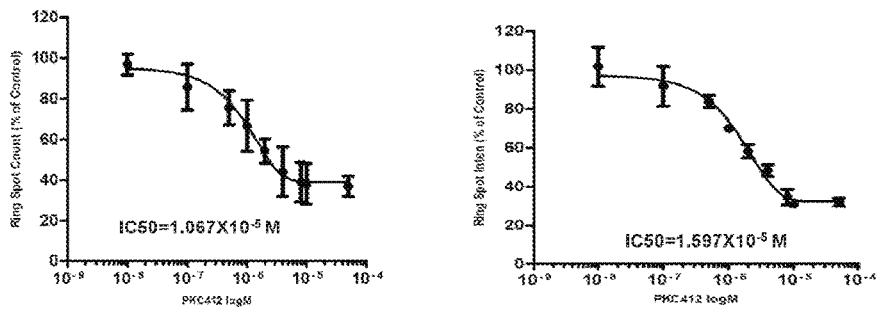
Fig. 6A
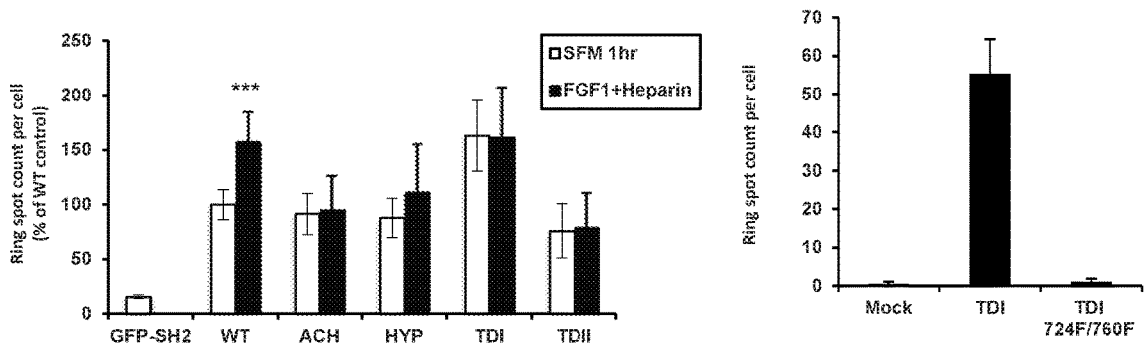
Fig. 6B
Fig. 6C pheophorbide a
(Pa)

HCl-N-Pa

Na-Pa

COMPOSITION AND METHOD FOR MODULATING FIBROBLAST GROWTH FACTOR RECEPTOR 3 ACTIVATION

BACKGROUND

Point mutations in the fibroblast growth factor receptor 3 (FGFR3) that cause constitutive activation of this receptor give rise to a variety of cancers and congenital skeletal dysplasias inherited as autosomal dominant traits. The skeletal dysplasias are characterized by varying degrees of skeletal deformities ranging from least to most severe as follows: hypochondroplasia (HCH), achondroplasia (ACH), severe achondroplasia with developmental delay and acanthosis nigricans (SADDAN), and thanatophoric dysplasia type 1 (TDI) and type 2 (TDII).

ACH is the most common form of genetic short-limbed dwarfism in humans. It is characterized by short stature with disproportionately short limbs, macrocephaly, characteristic faces with frontal bossing, midface hypoplasia, and exaggerated thoracolumbar kyphosis.

Several ACH mouse models have been established to study the roles of FGFR3 in skeletal development and disease. See Wang et al., Proc. Natl. Acad. Sci. USA 96:4455-4460; Chen et al., J. Clin. Invest. 104:1517-1525; Naski et al., Development 125:4977-4988; and Segev et al., Hum. Mol. Genet. 9:249-258. Yet, although these mouse models share some phenotypes with human ACH, not all of the human disease phenotypes have been fully described or examined in these mouse models.

Although there are several potential therapeutic strategies under development for FGFR3-activated diseases, no pharmaceuticals have been approved for FGFR3-activated skeletal dysplasias. See Jin et al., Hum. Mol. Genet. 21:5443-5455; Lorget et al., Am. J. Hum. Genet. 9:1108-1114; Garcia et al., Science Translational Medicine: 203ra124; Xie et al., Hum. Mol. Genet. 21:3941-3955; Yamashita et al., Nature 513:503-511; Matsushita et al., Endocrinology 156:548-554; and Komla-Ebri, et al., J. Clin. Invest. 126:1871-1874.

Clearly, there is a need to develop tools and methods for identifying agents that target overactive FGFR3 mutants and to identify therapeutics for disorders associated with overactive FGFR3 mutants.

SUMMARY

To meet the needs set out above, a method of inhibiting an overactive fibroblast growth factor receptor 3 (FGFR3) in a cell is disclosed. The method includes contacting the cell with a composition containing an effective amount of Pheophorbide a, Pyropheophorbide a, or an active derivative thereof.

In another aspect, a method is described herein for treating a disorder associated with an overactive FGFR3 in a subject by identifying a subject in need of treatment and administering to the subject a composition containing an effective amount of Pheophorbide a, Pyropheophorbide a, or an active derivative thereof.

In yet another aspect, described herein is a knock-in mouse, comprising one or two heterologous genomic nucleic acids, wherein the one or two heterologous nucleic acids each replaces a coding region of an endogenous Fgfr3 gene and is operably linked to an endogenous Fgfr3 promoter, the one or two heterologous nucleic acids, individually, encoding a human wild-type FGFR3 or a human FGFR3(G380R) mutant.

Further, described herein is a mammalian cell that contains a first exogenous nucleic acid encoding a human FGFR3 protein and a second exogenous nucleic acid encoding a fusion protein that includes a green fluorescent protein (GFP) and a FGFR3 effector protein. The cell expresses the human FGFR3 protein and the fusion protein, and the effector protein is capable of binding to an activated FGFR3.

In another aspect, described herein is a method of identifying a modulator of FGFR3 activation, comprising: providing a mammalian cell described herein, contacting the cell with a test agent, imaging the cell for cytoplasmic GFP signals, and obtaining a count of individual cytoplasmic GFP spots. Obtaining a count that is lower or higher than a control count indicates that the test agent is a modulator of FGFR3 activation.

Also disclosed is the use of a plant ethanol extract for inhibiting an overactive fibroblast growth factor receptor 3 (FGFR3), the plant belonging to the family Amaranthaceae, Sapotaceae, or Zingiberaceae.

Further, a composition for treating a disorder associated with an overactive FGFR3 is provided. The composition contains an effective amount of an ethanol extract of a plant belonging to the family Amaranthaceae, Sapotaceae, or Zingiberaceae.

The details of one or more embodiments are set forth in the accompanying drawing and the description below. Other features, objects, and advantages of the embodiments will be apparent from the description and drawing, and from the claims.

BRIEF DESCRIPTION OF THE DRAWINGS

The invention description below refers to the accompanying drawings, of which:

FIG. 5A shows schematics of control (top) and fusion constructs with *Renilla reniformis* green fluorescent protein (RrGFP) that interact with activated FGFR3. The src homology 2 domain (SH2) from SH2B (SEQ ID NO: 1) and the SH2 from PLCγ (SEQ ID NO: 2) are shown;

FIG. 5B shows the site of certain single nucleotide mutations in human FGFR3 that cause constitutive activation of this receptor;

FIG. 6A are plots of cell-based translocation assay data (see below), expressed as ring spot count (left panel) and ring spot intensity (right panel), as a percentage of control for SH2(SH2B)-RrGFP/TDI FGFR3 expressing U2OS cells treated with the indicated concentrations of PKC412;

FIG. 6B is a plot of ring spot count as a percentage of control for U2OS cells stably expressing SH2(SH2B)-RrGFP, WT FGFR3, or activated FGFR3 (ACH, HYP, TDI, and TDII) treated with serum-free medium (SFM) or with SFM, acidic fibroblast growth factor (aFGF), and heparin;

FIG. 6C is a plot of ring spot count per cell in cells transiently expressing SH2(SH2B)-RrGFP together with activated FGFR3 (TDI), or the TDI 724F/760F mutant that does not bind to SH2 domains;

FIG. 14 is a plot of body weight versus time for untreated WT, ACH/ACH or these mice treated with Pheophorbide a.

DETAILED DESCRIPTION

Figure 1A:
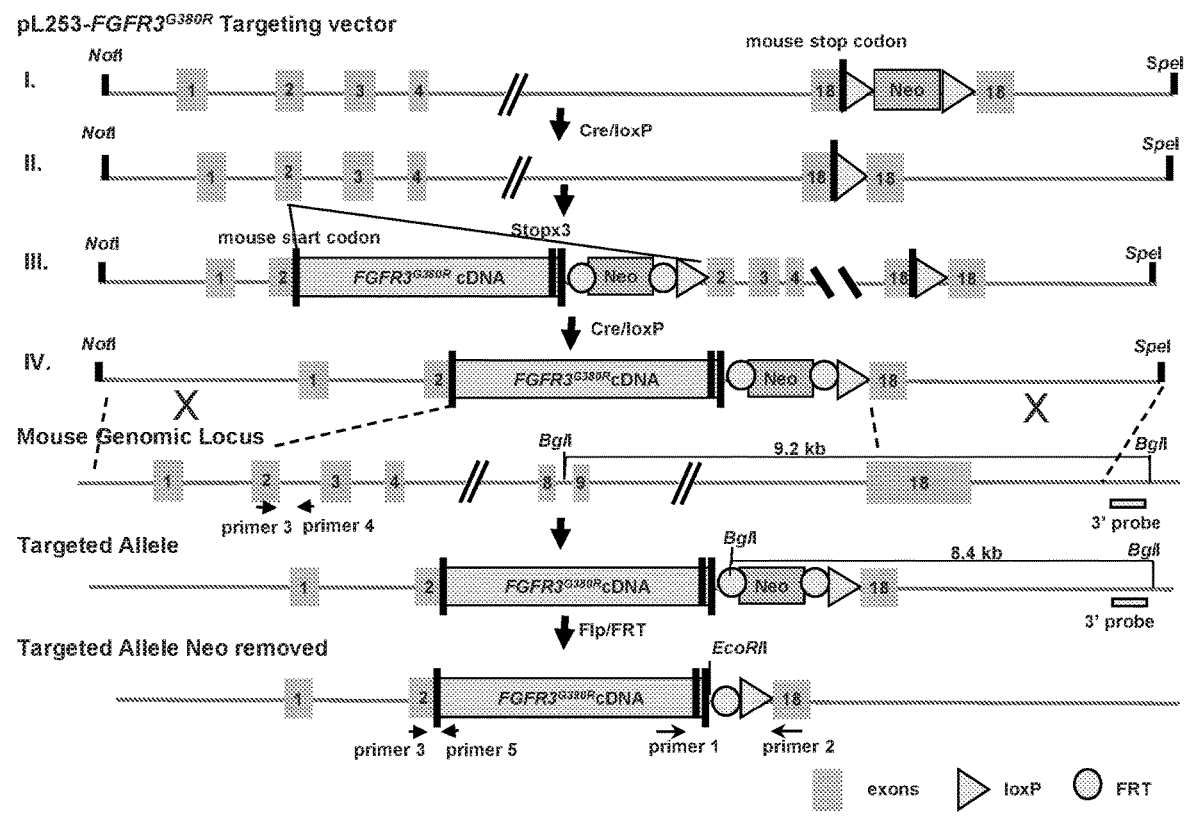
FIG. 1A is a schematic of the stepwise generation of ACH mice and human FGFR3 WT controls by introducing human FGFR3$^{G380R}$ cDNA or WT FGFR3 into the murine Fgfr3 locus. Generation of the targeting vector (Parts I-IV) and the final chromosomal structure of the murine Fgfr3 locus after the introduction of the human FGFR3$^{G380R}$ cDNA via gene targeting are shown.

Described herein is a method of inhibiting an overactive FGFR3 or treating a disorder associated with an overactive FGFR3 in a subject. The method includes identifying a subject in need thereof, and administering to the subject a composition containing an effective amount of Pheophorbide a or Pyropheophorbide a (or a functional derivative thereof).

The overactive FGFR3 can be overexpression of FGFR3 or an overactive FGFR3 mutant. The overactive mutant can be, for example, FGFR3(Y373C), FGFR3(G380R), FGFR3 (N540K), FGFR3(K650E), FGFR3(R248C), FGFR3 (S371C), FGFR3(Y373C), FGFR3(G375C), FGFR3 (G380R), FGFR3(N540K), FGFR3(K650M), FGFR3 (K650E), FGFR3(X807G), FGFR3(X807R), or FGFR3 (X807C).

The disorder can be a skeletal dysplasia or a cancer, e.g., achondroplasia, hypochondroplasia, severe achondroplasia with developmental delay and acanthosis nigricans (SADDAN), thanatophoric dysplasia type I, thanatophoric dysplasia type II, multiple myeloma, bladder cancer, cervical cancer, or any type of cancer associated with FGFR3 activation.

The composition can include purified or synthesized Pheophorbide a or Pyropheophorbide a. Alternatively, the composition can contain active derivatives of Pheophorbide a or Pyropheophorbide a, e.g., HCl-N-Pheophorbide a, Na-Pheophorbide a, HCl-N-Pyropheophorbide a, and Na-Pyropheophorbide a. The composition can also be an extract of a green plant or green algae (e.g., any plant or algae that carries out photosynthesis). In one embodiment, the plant is *Amaranthus viridis*.

Also described herein is a knock-in mouse. The mouse includes one or two heterologous genomic nucleic acids, wherein the one or two heterologous nucleic acids each replaces a coding region of an endogenous Fgfr3 gene and is operably linked to an endogenous Fgfr3 promoter, the one or two heterologous nucleic acids, individually, encoding a human wild-type FGFR3 or a human FGFR3(G380R) mutant. The mouse can contain both of the heterologous genomic nucleic acids, one of which encodes the FGFR3 (G380R) mutant, wherein the transgenic mouse has an externally dominant short stature, rounded head, short snout, and humpback, and skeletal abnormalities including rhizomelic dwarfism, rounded skull, and curvature of the cervical and upper thoracic vertebrae. The mouse can be generated using methods known in the art or described below.

Disclosed herein is a mammalian cell, comprising a first exogenous nucleic acid encoding a human FGFR3 protein and a second exogenous nucleic acid encoding a fusion protein that includes a green fluorescent protein (GFP) and a FGFR3 effector protein, wherein the cell expresses the human FGFR3 protein and the fusion protein, and wherein the effector protein is capable of binding to an activated FGFR3. In one embodiment, the effector protein is the Src homology 2 (SH2) domain of human SH2-B(3. The GFP can be from *Renilla reniformis*.

The human FGFR3 protein is a wild-type protein or an overactive mutant, e.g., FGFR3(Y373C), FGFR3(G380R), FGFR3(N540K), FGFR3(K650E), FGFR3(R248C), FGFR3 (S371C), FGFR3(Y373C), FGFR3(G375C), FGFR3 (G380R), FGFR3(N540K), FGFR3(K650M), FGFR3 (K650E), FGFR3(X807G), FGFR3(X807R), or FGFR3 (X807C). The cell containing an overactive FGFR3 mutant and an SH2-GFP fusion protein exhibits a punctate pattern of cytoplasmic GFP spots. Treating such a cell with an inhibitor of FGFR3 activity reduces or eliminates the cytoplasmic GFP spots. Conversely, treating the cell with a substance that further activates the FGFR3 will result in an increase in cytoplasmic GFP spots.

The mammalian cell can be used to identify agents that modulate FGFR3 activation. Thus, described herein is a method of identifying a modulator of FGFR3 activation that includes providing a mammalian cell described above, contacting the cell with a test agent, imaging the cell for cytoplasmic GFP signals, and obtaining a count of individual cytoplasmic GFP spots, i.e., ring spot counts. Obtaining a count that is lower or higher than a control count indicates that the test agent is a modulator of FGFR3 activation. If the count is lower than the control count, it indicates that the test agent is an inhibitor of FGFR3 activation. Obtaining a count that is higher than the control count indicates that the test agent is an activator of FGFR3 activation.

The test agent can be a plant, algae extract, or other nature complex mixture extracts, small molecule compound, peptide, protein, antibody, nucleic acid molecule, peptidomimetic, or peptoid.

Also within the scope of the invention is the use of a plant ethanol extract for inhibiting an overactive FGFR3. The plant can be, but is not limited to, a member of the family Amaranthaceae, Sapotaceae, or Zingiberaceae. In a specific embodiment, the ethanol extract is from *A. viridis*. In a particular embodiment, the extract includes Pheophorbide a, Pyropheophorbide a, or active derivatives thereof.

A composition for treating a disorder associated with an overactive FGFR3 is also disclosed. The composition contains an effective amount of an ethanol extract of a plant belonging to the family Amaranthaceae, Sapotaceae, or Zingiberaceae. In a specific aspect, the ethanol extract is from *A. viridis*. The extract can include Pheophorbide a, Pyropheophorbide a, or their active derivatives.

In addition, a composition for treating a disorder associated with an overactive FGFR3 is disclosed where the composition contains an ethanol extract from the plant *A. viridis* prepared by the steps of drying and chopping the plant, subjecting the chopped plant material to 95% ethanol reflux extraction, concentrating the ethanol extract, fractionating the extract on a Diaion HP-20 column, eluting stepwise with 100% $H_2O$ (fraction 1), 50% v/v ethanol in $H_2O$ (fraction 2), 100% ethanol (fraction 3), 50% (v/v) ethanol in ethyl acetate (fraction 4), and 100% ethyl acetate (fraction 5), and collecting fraction 4.

The steps for preparing the ethanol extract from *A. viridis* can further include subjecting fraction 4 to forward-phase silica gel column chromatography using hexane in ethyl acetate and ethyl acetate in methanol as the mobile phases.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications cited herein are hereby incorporated by reference in their entirety.

EXAMPLES

Example 1

Knock-In Human FGFR3 Achondroplasia Mutation as a Mouse Model for Human Skeletal Dysplasia Generation of $FGFR3^{ACH}$ and $FGFR3^{WT}$ Mice A gene-targeting approach was employed to generate $FGFR3^{ACH}$ mice by replacing the mouse Fgfr3 with human FGFR3 cDNA carrying the ACH mutation ($FGFR3^{ACH}$) under the full control of the endogenous mouse Fgfr3 promoter, intron 1, and 5' and 3' untranslated regions. See FIG. 1. Human WT FGFR3 ($FGFR3^{WT}$) cDNA was also introduced into Fgfr3 through the same approach to generate control mice for comparison.

A targeting vector for the expression of human $FGFR3^{G380R}$ was developed as follows. A DNA fragment carrying the entire mouse Fgfr3 locus derived from the 129S7 mouse strain was retrieved from a bacterial artificial chromosome clone (Geneservice, Cambridge, UK) and cloned into the PL253 plasmid. See FIG. 1A I. A loxP-flanked neomycin resistance cassette was inserted into exon 18 after the stop codon through recombination, and the neomycin resistance cassette was removed through Cre/loxP excision, leaving behind a loxP sequence. See FIG. 1A, Part II. A DNA fragment containing (i) the human mutant FGFR3 cDNA encoding the $FGFR3^{G380R}$ protein, (ii) three translational stop codons, (iii) a neomycin resistance cassette flanked by FRT sites, and (iv) a loxP sequence was inserted after the mouse exon 2 start codon. See FIG. 1A, Part III. The region of mouse Fgfr3 between exons 2-18 was removed by Cre/loxP excision. See FIG. 1A, Part IV. The resulting targeting vector was used to replace the WT allele of Fgfr3 in 129Sv mouse embryonic stem cells. See FIG. 1A, Part V.

Clones of the embryonic stem cells containing the targeted allele were identified by Southern blot analysis via digestion of genomic DNA with BglI and hybridization with a 0.5 kb 3' oligonucleotide probe generated by PCR. See FIG. 1A, Parts V and VI. Embryonic stem cells carrying the targeted allele showed the presence of a 8.4 kb BglI fragment, confirming correct targeting.

Figure 1B:
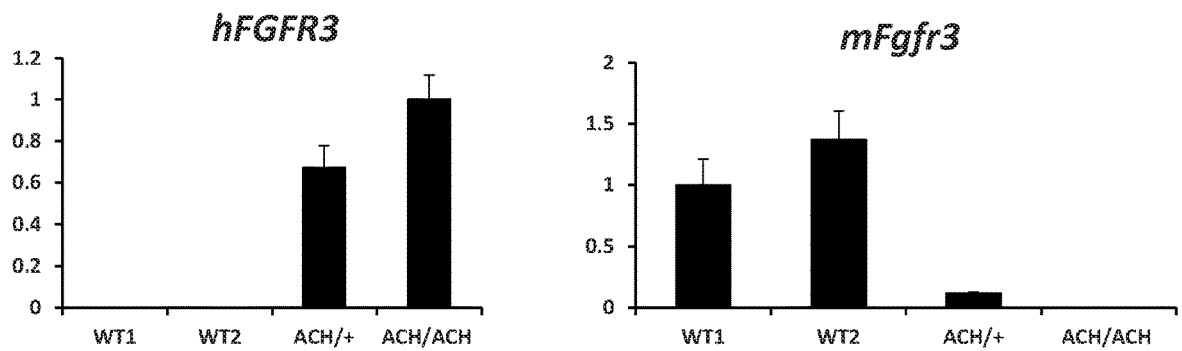
FIG. 1B are plots of relative mRNA expression levels of hFGFR3 (left panel) and mFgfr3 (right panel) in the hind limbs of wild-type (WT1, WT2), ACH heterozygotes (ACH/+) and homozygotes (ACH/ACH) mice. Values are relative mRNA expression normalized to GAPDH.

The neomycin resistance cassette in the identified stem cells was removed by Flp/FRT excision, and these cells were then analysed by PCR with primers against the 3' end of human FGFR3 cDNA and exon 18 of mouse Fgfr3, followed by EcoRI digestion of the PCR products. A 528 bp PCR product was amplified from genomic DNA isolated from the stem cells without the neomycin resistance cassette. This PCR product produced a 328 bp and a 254 bp fragment upon digesting it with EcoRI. The final chromosomal structure of the murine Fgfr3 locus after the introduction of the human FGFR3$^{G380R}$ cDNA via gene targeting with and without the neomycin resistance cassette are shown in FIG. 1A, Part VI and Part VII, respectively.

The stem cells carrying the targeting vector without the neomycin resistance cassette were injected into C57BL/6J blastocysts following established procedures. The resulting chimeric mice were crossed with 129Sv females to enable germline transmission. Heterozygotes were used to maintain the strain and to provide experimental pairs.

PCR amplification analysis was performed on genomic DNA isolated from WT and FGFR3$^{ACH}$ mice to confirm their genotypes. A 1067 bp PCR product was amplified from the mouse Fgfr3 locus in wild-type animals using primers 3 (5'-CCT CCG GAG TAA CTC AGT GC-3'; SEQ ID NO:27) and 4 (5'-ACA ACT TAC CGA GCG AAA GC-3'; SEQ ID NO:28). See FIG. 1A, Part V. On the other hand, a 506 bp PCR product was amplified from the human FGFR3$^{G380R}$ targeted allele with primers 3 and 5 (5'-GCA CAC TGA AGT GGC ACA GT-3'; SEQ ID NO: 29). See FIG. 1A, Part VII.

Micro-Computed Tomography (Micro-CT)

Mice were euthanized and dissected tissues were fixed in 4% (w/v) paraformaldehyde overnight. After transferring the specimens to 70% (v/v) ethanol, trabecular bone of the distal femur metaphysis was analysed by three-dimensional micro-CT using a Skyscan 1076 3D system in the Taiwan Mouse Clinic, following standard protocols. The following scanning parameters were chosen: image pixel size: 9 µm, X-ray voltage: 50 kV, X-ray current: 140 µA, filter: A1 0.5 mm, exposure: 3300 ms, rotation step: 0.8°, frame averaging: 2, tomographic rotation: 180°. Cross-sections were reconstructed using NRecon software (Bruker). The parameters were as follows: smoothing: 0, ring artefacts reduction: 6, beam-hardening correction: 20%, change dynamic image range: 0.015-0.07.

Histology, Histochemistry, and Immunohistochemistry

Bone tissues were fixed with 4% (w/v) paraformaldehyde, and 5 µm sections were prepared and examined with Masson's trichrome stain. For immunohistochemistry, the fixed bone tissues were then decalcified in 10% (w/v) EDTA for 2 weeks. The sections were de-paraffinized and retrieved by incubation in 0.05% (w/v) trypsin at 37° C. for 15 min. After treatment with 3% (v/v) H$_2$O$_2$ and blocking with 5% (v/v) normal goat serum, sections were incubated with primary antibodies at 4° C. overnight. Phospho-FGFR3 antibody (Cell Signalling, Danvers, Mass., USA) was used to detect FGFR3 activation, and the sections were then incubated with anti-rabbit secondary antibody (VECTASTAIN® ABC system, Vector Labs, Burlingame, Calif., USA) and visualised using 0.1% (w/v) 3,3'-diaminobenzidine. Images were captured using standard light microscopy (Zeiss, Oberkochen, Germany)

Primary Chondrocyte Culture

Primary chondrocytes were isolated and cultured essentially as described in Gosset et al., Nature Protocols 3:1253-1260 with several modifications. Briefly, connective tissue-free epiphysis region was dissected from day 10 postnatal mice and then digested with type II collagenase (Worthington, Lakewood, N.J., USA) overnight. Chondrocytes were filtered through a 70-mm nylon mesh (BD Biosciences, San Jose, Calif., USA) and then cultured in DMEM containing 10% (v/v) FCS. To avoid transformation of the cell phenotype, only primary cells were used for experiments.

Cell Proliferation Assay

Chondrocyte proliferation was assessed using an iCEL-Ligence™ real-time cell analyzer (Acea Biosciences, San Diego, Calif., USA, distributed by Roche Diagnostics, Basel, Switzerland). Briefly, 10,000 viable cells/well were seeded in an 8-well plate in complete medium and grown for 10 days. Changes in adhesion and spreading of the cells were continuously recorded for 15 days using the iCELLigence™ system. The growth medium was exchanged every 2 days. Data were expressed as a graph of cell index values during the exponential phase.

Skeletal Preparation

Skinned and eviscerated newborn mice were fixed overnight in 95% (v/v) ethanol, followed by overnight incubation with acetone. The specimens were then stained with Alcian blue 8GX (0.05%, w/v) (Sigma-Aldrich, St. Louis, Mo., USA) for 72 h, after which they were dehydrated in 95% (v/v) ethanol for 24 h. The skeletons were incubated in 1% (w/v) KOH until the bone was visible. The skeletons then were further stained with alizarin red (0.005%, w/v) (Sigma-Aldrich) for 24 h. Specimens were cleared in a solution of 35% ethanol, 50% glycerol, and 15% water (all percentages represent v/v) to remove excess stain, and then preserved in 100% glycerol.

Mice

Mice were housed in a temperature- and humidity-controlled room with a 12-h light/12-h dark cycle under specific pathogen-free conditions. All animal protocols were approved by the Institutional Animal Care and Utilization Committees, Academia Sinica, Taiwan (Protocol #14-12-795). The investigation conformed to the Guide for the Care and Use of Laboratory Animals published by the US National Institutes of Health.

Quantitative Reverse Transcriptase Polymerase Chain Reaction (qRT-PCR)

Total RNA from the left hind-limb of neonatal mice was isolated, converted to DNA, and subjected to qRT-PCR. Expression data were normalized to GAPDH mRNA levels. Gene-specific primer sequences are listed below.

Mouse Fgfr3: forward sequence, 5'-TGCGGTGCCTT-CACAGA-3' (SEQ ID NO: 3); reverse sequence, 5'-ACTTGGACCTCTCCGTG-3' (SEQ ID NO: 4); Human FGFR3: forward sequence, 5'-GCT-GAGGACACAGGTGTG-3' (SEQ ID NO: 5); reverse sequence, 5'-CACTCCCTCCATCTCCTG-3' (SEQ ID NO: 6); GAPDH: forward sequence, 5'-CCAGAACAT-CATCCCTGCAT-3' (SEQ ID NO: 7); reverse sequence, 5'-GTTCAGCTCTGGGATGACCTT-3' (SEQ ID NO: 8).

The level of mRNA expression of targeted human FGFR3$^{G380R}$ and endogenous mouse Fgfr3 in the heterozygous FGFR3$^{G380R}$, homozygous FGFR3$^{G380R}$, and WT mice was determined by RT-PCR using the primers described above and normalized to GAPDH mRNA expression levels. The results, shown in FIG. 1B, confirmed that human FGFR3$^{G380R}$ was expressed only in the heterozygous FGFR3$^{ACH/+}$ mice and the homozygous FGFR3$^{ACH/ACH}$ mice and not in wild type littermates. Conversely, murine Fgfr3 expression was only detected in wild-type litter mates and a minor amount in heterozygous FGFR3$^{ACH/+}$ mice.

Bone Length Measurement

Femurs of mice were dissected and the flesh was removed. The lengths of the femurs were measured using a millimetre-scale calliper ruler.

Statistical Analysis

A two-tailed Student's t-test was used to test for differences between groups. A p value less than 0.05 was considered to be statistically significant. Chi-square goodness-of-fit tests (2 degrees of freedom) were used to test for departures from Mendelian expectations for the genotypes of FGFR3$^{ACH}$ mice generated from heterozygous breeding pairs.

Results

Survival and Growth Rates

Figure 2A:
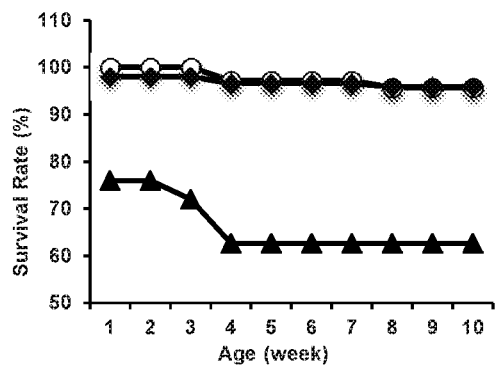
FIG. 2A shows the deviation from expected Mendelian ratios upon crossing heterozygote ACH/+ mice (upper panel). The lower panel shows a plot of survival % versus age for WT, ACH/+, and ACH/ACH mice. Open circles=WT, filled circles=ACH/+, and filled triangles=ACH/ACH.
Figure 2B:
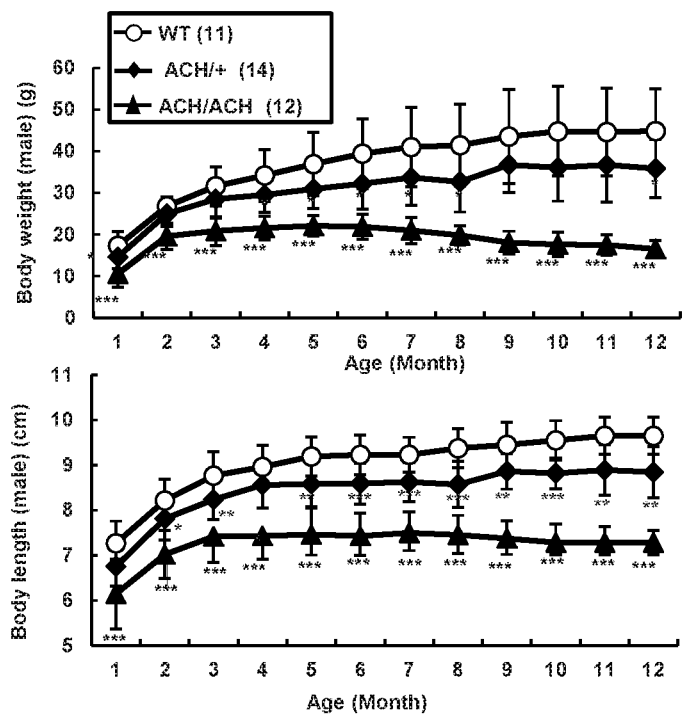
FIG. 2B are plots of body weight versus age (left panel) or body length versus age (right panel) for WT, ACH/+, and ACH/ACH mice. *p-value<0.05, p-value<0.01, *p-value<0.001) by two-tailed Student's T-test.

FGFR3$^{ACH/ACH}$ mice had a significantly lower survival rate at birth relative to expectations and a higher mortality rate before 4 weeks of age, as compared to FGFR3$^{ACH/+}$ and WT mice. See FIG. 2A. The majority of FGFR3$^{ACH}$ mice died at around 1 year of age. Mean body weights and body lengths were decreased in both FGFR3$^{ACH/+}$ and FGFR3$^{ACH/ACH}$ mice relative to WT mice. See FIG. 2B. FGFR3$^{ACH/+}$ mice exhibited intermediate body weights and lengths between those of the WT and FGFR3$^{ACH/ACH}$ mice, indicating a dose-dependent effect of activated FGFR3$^{G380R}$. See FIG. 2B.

Skeletal Abnormalities in Newborn FGFR3$^{ACH}$ Mice

The features of human ACH patients can be readily identified clinically and radiologically at birth. At birth, there were no obvious differences in appearance between FGFR3$^{ACH/+}$ or FGFR3$^{ACH/ACH}$ mice, collectively termed FGFR3$^{ACH}$, and their WT littermates. An analysis of the bone structure of newborn FGFR3$^{ACH}$ mice showed proximal limb shortening with relatively normally sized trunks. Femur length was reduced by 15% in FGFR3$^{ACH/+}$ mice and 42% in FGFR3$^{ACH/ACH}$ mice, as compared to WT mice. A closer view of skull structure revealed that the skull was rounded and the calvarial bones were distorted in FGFR3$^{ACH}$ mice, due to a positional shift and compression of the frontal and parietal bones. The jugum limitans, i.e., the cranial suture that separates the frontal and nasal bones, was absent in FGFR3$^{ACH}$ mice. The metopic sutures, which line the midline between the two nasal bones, were unilaterally fused or partially absent in FGFR3$^{ACH}$ mice. Thus, newborn FGFR3$^{ACH}$ mice exhibited premature suture closure and abnormal skull shapes. Furthermore, newborn FGFR3$^{ACH}$ demonstrated a shorter intervertebral distance between cervical vertebrae and a narrower rib cage as compared to WT mice. These phenotypes are similar in many respects to the skeletal deformities in human ACH newborns, and the bone abnormalities are more evident in FGFR3$^{ACH/ACH}$ mice than in FGFR3$^{ACH/+}$ mice.

Pronounced Skeletal Abnormalities in FGFR3$^{ACH}$ Mice During Postnatal Development The dwarfism phenotypes gradually became evident in FGFR3$^{ACH}$ mice. Dominant short stature, rounded head, short snout, and kyphosis (humpback) phenotypes were readily observed in FGFR3$^{ACH}$ mice at 10 days to 1 month of age. All FGFR3$^{ACH/ACH}$ mice developed kyphosis phenotypes at around 2 weeks of age, and about 90% of FGFR3$^{ACH/+}$ mice developed kyphosis phenotypes before 1 month of age. In addition, protrusion of the lower incisors was observed in FGFR3$^{ACH}$ mice as a result of changes in the skull affecting the alignment of the incisors.

By contrast, the control FGFR3$^{WT/+}$ or FGFR3$^{WT/WT}$ mice expressing non-mutated human FGFR3 showed identical external phenotypes to those of WT. Further, the growth rates of WT, FGFR3$^{WT/+}$, and FGFR3$^{WT/WT}$ mice were the same.

Two-dimensional micro-computed tomography (micro-CT) was used to examine the skeletal abnormalities in FGFR3$^{ACH}$ mice. The skeletal bone revealed dwarfism, rounded skulls, and severe curvature of the cervical and upper thoracic vertebrae in FGFR3$^{ACH}$ mice. FGFR$^{ACH/ACH}$ mice exhibited more severe phenotypes compared with those of FGFR3$^{ACH/+}$ mice. Furthermore, these phenotypes became more pronounced in older mice, based on comparison among the phenotypes of 1-, 4-, and 12-month-old mice. Close observation of the skulls and vertebrae of FGFR3$^{ACH}$ mice revealed shortened snouts, dome-shaped skulls, and almost completely folded upper thoracic vertebrae in FGFR$^{ACH/ACH}$ and older FGFR$^{ACH/+}$ mice. The severities of these phenotypes were more consistent among FGFR3$^{ACH/ACH}$ mice, as compared with FGFR3$^{ACH/+}$ mice, as evidenced by the smaller variation in the body lengths of FGFR3$^{ACH/ACH}$ mice compared with that of FGFR3$^{ACH/+}$ mice. See FIG. 2B. Clearly, the variation in the severities of the short snout, rounded-head, and kyphosis phenotypes is represented in the body length.

Patients with ACH present with rhizomelic (short-limbed) dwarfism. This phenotype was reproduced in the FGFR3$^{ACH/+}$ mice, which showed a 22% shortening of femur length along with a 7.1% shortening of body length at 1 month of age, as compared to the corresponding measurements in WT mice. The limbs of FGFR3$^{ACH/+}$ mice were disproportionately shortened relative to body length. In addition, the femurs of these animals were short, curved, and thick, with widened diaphyses and flared metaphyses, phenotypes which are very similar to those observed in ACH patients.

Altered Chondrocyte Proliferation and Differentiation in FGFR3$^{ACH}$ Mice

Figure 3A:
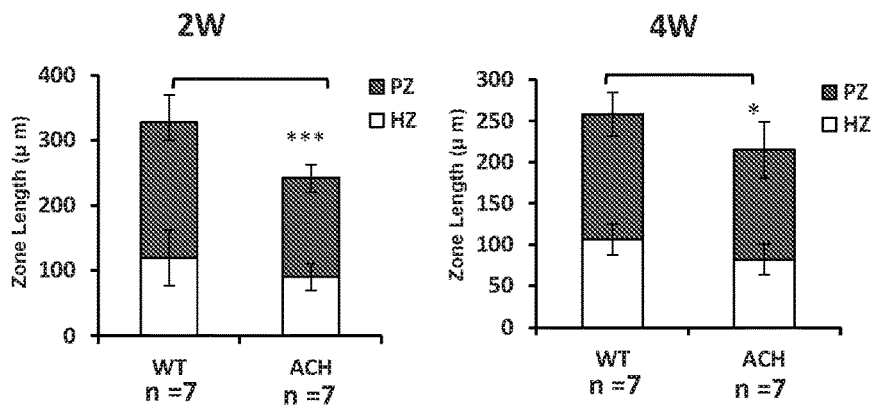
FIG. 3A are bar graphs of measurements of the heights of the proliferative zone (PZ) and hypertrophic zone (HZ) of the distal femoral growth plates of FGFR3$^{ACH}$ (ACH) mice and WT mice at 2 and 4 weeks of age. Data shown are mean values±SD. *p<0.05; ***p<0.001.
Figure 3B:
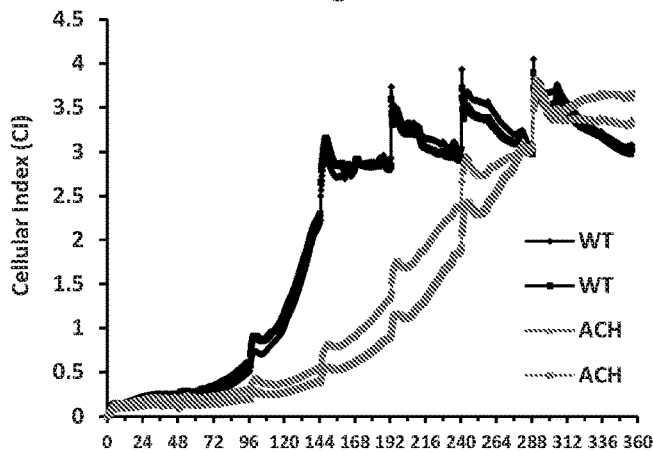
FIG. 3B is a plot of cellular index versus time for chondrocytes from wild-type (WT) and FGFR3$^{ACH/ACH}$ (ACH) mice analysed using an iCELLigence™ real-time cell analysis system.

As mentioned above, femur length is significantly reduced in FGFR3$^{ACH}$ mice. A histological analysis of the distal femur from WT and FGFR3$^{ACH}$ mice at different developmental stages was performed to more closely examine defects in the long bones of FGFR3$^{ACH}$ mice. The epiphyseal structure was similar between WT and FGFR3$^{ACH}$ mice at birth. The secondary ossification center was readily formed in WT mice at 1 week of age, whereas its formation was markedly delayed in FGFR3$^{ACH}$ mice, suggesting a delay in chondrocyte terminal differentiation. In endochondral ossification, chondrocytes sequentially transit through resting, proliferating, prehypertrophic, and hypertrophic stages. The FGFR3$^{ACH}$ mice showed good development of each stage. However, the growth plates were significantly shorter in FGFR3$^{ACH}$ mice with a shorter proliferative zone at 2, 4, and 8 weeks of age. See FIG. 3A. This resulted from a reduction in the number of proliferative chondrocytes, indicating that chondrocyte proliferation was compromised in FGFR3$^{ACH}$ mice. See FIG. 3B.

Despite the shorter proliferative zone, the arrangement of chondrocyte columns in the growth plate remained normal in FGFR3$^{ACH}$ mice before 2 weeks of age. At 4 and 8 weeks of age, an increased amount of space between chondrocyte columns was observed in FGFR3$^{ACH}$ mice. FGFR3$^{ACH}$ mice also demonstrated higher FGFR3 phosphorylation in chondrocytes of growth plates, and the primary chondrocytes had lower proliferation rates compared with those from WT mice. These results suggest that FGFR3 activation inhibited chondrocyte proliferation in FGFR3$^{ACH}$ mice.

Altered Bone Formation in FGFR3$^{ACH}$ Mice

Reduced growth of the longitudinal trabecular bone was observed in the distal femoral metaphysis of FGFR3$^{ACH}$ mice at several stages of postnatal development. Furthermore, the expression of osteocalcin, which is associated with the early stages of matrix ossification, was increased in the chondrocytes of the maturing zone and hypertrophic zone of the distal femur of FGFR3$^{ACH}$ mice at 2 weeks of age. A reduced hypertrophic zone was observed in FGFR3$^{ACH}$ mice at 8 weeks of age. The bone-forming process was clearly disturbed in FGFR3$^{ACH}$ mice. To determine the structure of trabecular bone, we performed a micro-CT analysis. Three-dimensional images of the distal femoral metaphysis showed a lower bone volume with thinner and fewer trabecular bones and larger intertrabecular spaces in newborn and 1-year-old FGFR3$^{ACH}$ mice, as compared to WT mice. A histomorphometric analysis of bone formation showed that the trabecular bone volume (BV/TV), trabecular thickness (Tb.Th), and trabecular number (Tb.N) were decreased, along with an increased trabecular separation (Tb.Sp) and structure model index (SMI) in the distal femoral metaphysis of FGFR3$^{ACH}$ mice compared with WT mice at birth and at 1 year of age, as shown below in Table 1.

TABLE 1

Structural parameters of distal femur trabecular bone in newborn mice

| | BV/TV (%) | Tb•Th (mm) | Tb•Sp (mm) | Tb•N (1/mm) | SMI |
|---|---|---|---|---|---|
| newborn | | | | | |
| WT (n = 3) | 43.16 ± 1.85 | 0.076 ± 0.007 | 0.086 ± 0.006 | 5.718 ± 0.35 | 1.487 ± 0.24 |
| ACH/ACH (n = 3) | 15.76 ± 3.93*** | 0.058 ± 0.011 | 0.17 ± 0.045 | 2.74 ± 0.71*** | 2.436 ± 0.26** |
| 1 year old | | | | | |
| WT (n = 4) | 5.22 ± 0.51 | 0.079 ± 0.010 | 0.383 ± 0.047 | 0.661 ± 0.087 | 2.569 ± 0.20 |
| ACH/ACH (n = 3) | 2.74 ± 1.08* | 0.069 ± 0.003 | 0.378 ± 0.075 | 0.402 ± 0.169 | 2.87 ± 0.37 |

WT: wild-type littermates;
ACH/ACH: FGFR3$^{ACH/ACH}$ mice.
BV/TV: trabecular bone volume/tissue volume;
Th•Th: trabecular thickness;
Th•Sp: trabecular separation;
Tb•N: trabecular number;
SMI: structure model index.
Each value is expressed as the mean ± SD (all groups n = 3).
*p < 0.05;
**p < 0.01;
***p < 0.001.

Furthermore, fewer osteoblasts and osteoclasts were observed in the femurs of FGFR3$^{ACH}$ mice at 1 year of age, suggesting that the bone turnover rate might be altered in FGFR3$^{ACH}$ mice.

A comparison of skeletal phenotypes between human achondroplasia and the ACH mouse models described above is summarised below in Table 2.

TABLE 2

Similarity of skeletal features found in human achondroplasia and observed in achondroplasia mouse models.

| Skeletal features of human achondroplasia | Tg mFgfr$^{ACH}$ | KI mFgfr3$^{ACH}$ | Tg hFGFR3$^{ACH}$ | KI hFGFR3$^{ACH}$ |
|---|---|---|---|---|
| Rhizomelic dwarfism at birth | NS | NS | At birth$^a$ | At birth |
| Large head with frontal bossing, mid-face hypoplasia at birth | 21 days | 10 days | At birth | At birth |
| Craniosynostosis at birth | ND | ND | ND | At birth |
| Low bone density in adolescent and adult | ND | ND | ND | At birth |
| Homozygous ACH patients are stillborn or die during the neonatal period | ND | ND | Die soon after birth | A higher mortality rate at birth |
| Thoracic kyphosis by 4 months | 1 month | 5 weeks | ND | 1 month |
| Narrow growth plate | 10 days | 1 month | At birth | 1 month |

Tg mFgfr3$^{ACH}$, transgenic mice expressing mouse Fgfr3$^{G374R}$ using the type II collagen promoter and enhancer sequences (see Naski et al., Development 125:4977-4988.
KI mFGFR3$^{ACH}$, knock-in gene targeting mouse Fgfr3$^{G374R}$ (see Wang et al., Proc. Natl. Acad. Sci. USA 96:4455-4460).
Tg hFGFR3$^{ACH}$, transgenic mice expressing human FGFR3$^{G380R}$ using the mouse Fgfr3 promoter (see Segev, O. et al., Hum. Mol. Genet. 9:249-258).
KI hFGFR3$^{ACH}$, knock-in gene targeting human FGFR3$^{G380R}$ described above.
ND, not described;
NS, not significant.
$^a$The time point when the specific phenotype was first observed in each ACH mouse model.

Example 2

A Cell-Based Translocation Assay System for Identifying FGFR3 Modulators

A cell-based protein translocation system was established for identifying potential therapeutic natural compounds for the treatment of diseases associated with FGFR3 activation.
Plasmid Construction and Site-Directed Mutagenesis The full-length cDNA for *Renilla reniformis* green fluorescent protein (RrGFP) was amplified by polymerase chain reaction (PCR) and subcloned into the pcDNA3.1/Hygro expression vector (Invitrogen) using NotI and XbaI sites. Src homology domain 2 (SH2) proteins fused to the N-terminus of RrGFP were generated by amplifying the SH2 domain of human SH2Bβ and the two SH2 domains of human PLCγ from intron-containing genomic DNA and subcloning them into BamHI and NotI sites in the RrGFP expression vector. See FIG. 5A. Full-length cDNA for human FGFR3 (OriGene, Rockville, Md., USA) was subcloned into the BamHI and XbaI sites of the pcDNA3.1 expression vector (Invitrogen). Mutations were introduced into FGFR3 by oligonucleotide-directed mutagenesis using the QuikChange Site-Directed Mutagenesis kit (Stratagene, La Jolla, Calif., USA). The mutagenic oligonucleotides used are as follows: Y373C (TDI), (forward) 5'-CGAGGCGGG CAGTGTGTGTGCAGGCAT-3' (SEQ ID NO: 9) and (reverse) 5'-ATGCCTGCA CACACACTGCCCGCCTCG-3 (SEQ ID NO: 10); G380R (ACH), (forward) 5'-GCA TCCTCAGCTACAGGGTGGGCTTCTTC-3' (SEQ ID NO: 11) and (reverse) 5'-GAA GAAGCCCACCCTGTAGCT-GAGGATGC-3' (SEQ ID NO: 12); N540K (HYP), (forward) 5'-GGAAACACAAAAACATCAT-CAAACTGCTGGGCGCC-3' (SEQ ID NO: 13) and (reverse) 5'-GGCGCCCAGCAGTTTGAT-GATGTTTTTGTG TTTCC-3' (SEQ ID NO: 14); K650E (TDII), (forward) 5'-CCTCGACTACTACAAG GAGACAACCAACGGCCG-3' (SEQ ID NO: 15) and (reverse) 5'-CGGCCGTTGG TTGTCTCCTTGTAGTAGTCGAGG-3' (SEQ ID NO: 16). All plasmids were verified by DNA sequencing.
Cell Culture and Transfections The U2OS human osteosarcoma cell line was maintained in McCoy's 5A medium (complete medium) (Invitrogen, Carlsbad, Calif., USA) supplemented with 10% fetal bovine serum (FBS) in a humidified incubator at 37° C. and 5% CO$_2$. For transient assays, plasmids encoding RrGFP, SH2

(SH2B)-RrGFP, or SH2(PLCγ)-RrGFP fusion proteins were transfected into U2OS cells the day before performing assays. U2OS cells stably expressing SH2(SH2B)-RrGFP were generated by transfecting them with plasmids encoding SH2(SH2B)-RrGFP fusion protein and selecting in the presence of 400 µg/ml Hygromycin B (Invitrogen) for 2 weeks. Thereafter, individual positive clones were sorted by fluorescence-activated cell sorting (FACS) and selection was continued to yield individual transfected cell lines. A U2OS cell line stably expressing SH2(SH2B)-RrGFP was used for subsequent transfection with FGFR3. Plasmids encoding the FGFR3 forms described above, i.e., WT, TDI, ACH, HYP, and TDII, or empty expression vector were transfected into the U2OS SH2(SH2B)-RrGFP stable cell line and selected with 800 µg/ml G418 (Sigma-Aldrich, St. Louis, Mo., USA) for 2 weeks. All transfections in U2OS cells were carried out with Effectene (Qiagen, Hilden, Germany) according to the manufacturer's instructions.

Immunoprecipitation and Immunoblotting

Stable cell lines expressing both FGFR3 and SH2 (SH2B)-RrGFP were lysed in lysis buffer (50 mM Tris-HCl pH 8.0, 150 mM NaCl, 5 mM EDTA, 0.5% NP-40) supplemented with protease inhibitor cocktail (Roche, Mannheim, Germany). For immunoprecipitation experiments, cell lysates were pre-cleared with protein A/G PLUS-Agarose (sc-2003; Santa Cruz Biotechnology, Santa Cruz, Calif., USA) and then incubated with 2 µg of a polyclonal anti-FGFR3 antibody (C-15; Santa Cruz Biotechnology) for 1 h at 4° C. Protein A/B beads were then added and incubated overnight at 4° C. The immunoprecipitated samples were washed four times with lysis buffer and analyzed by immunoblotting using anti-FGFR3 (C-15), anti-RrGFP (1-233; Santa Cruz Biotechnology), and anti-phosphotyrosine (4G10; Millipore, Mass., USA) antibodies. For experiments not requiring immunoprecipitation, lysates were immunoblotted with anti-FGFR3 (C-15), anti-RrGFP (1-233), anti-pFGFR3 (3471; Cell Signaling, Beverly, Mass., USA), anti-PLCγ (2822; Cell Signaling), anti-pPLCγ (2821; Cell Signaling), anti-ERK1 C-16 (SC-123; Santa Cruz Biotechnology), anti-ERK1/2 Thr220/Thr204 (9101; Cell Signaling), anti-PI3K p85 (#4292, Cell Signaling), anti-pPI3K p85 alpha Tyr 508 (Sc-123, Santa Cruz), anti-STATS 3H7 (#9358, Cell Signaling), anti-pSTAT5 Tyr694 (#9359, Cell Signaling) or anti-β-actin (MBA1501; Millipore) antibodies, followed by detection using enhanced chemiluminescence (ECL; Amersham Biosciences, Little Chalfont, Buckinghamshire, UK).

Microscopy and Immunofluorescence Staining

U2OS cells stably expressing both the SH2(SH2B)-RrGFP fusion protein and various activated FGFR3 mutants were grown on glass chamber slides. The culture medium was replaced with serum-free medium for assay of kinase inhibition by PKC412, and live cells were imaged on an UltraView inverted confocal microscope (Perkin Elmer, Mass., USA). PKC412 was prepared as a 6% (w/w) stock in DMSO. Live-cell imaging was performed at 37° C. under humidified conditions in a 5% $CO_2$ incubator. For immunofluorescence staining, cells grown on chamber slides were fixed with 3.6% paraformaldehyde in phosphate-buffered saline (PBS) and stained with a rabbit polyclonal anti-FGFR3 antibody mentioned above. The primary antibody was detected with a rhodamine-conjugated anti-rabbit IgG secondary antibody (Jackson ImmunoResearch, Baltimore, Md., USA). Images were collected with a LSM510 META confocal microscope (Carl Zeiss MicroImaging, Inc., Thornwood, N.Y., USA)

Sample Preparation

For high-content screening, all steps of sample-plate preparation, including compound treatment, fixation and plate washing, were fully automated and were performed using a Bio-Tek EL405uv system (Bio-Tek Instruments, Inc., Winooski, Vt., USA). U2OS cells stably expressing TDI FGFR3 and SI-12-RrGFP were seeded at a density of $4 \times 10^3$ cells/well in black 96-well Packard Viewplates, incubated overnight in complete medium at 37° C. in a $CO_2$ incubator, and then transferred to 100 µl serum-free medium containing PKC412 or plant extract. The final DMSO concentration was 1%. After incubating for 1 hour at 37° C. in a $CO_2$ incubator, cells were fixed with 4.5% formaldehyde and cell nuclei were labeled with a 2 µg/ml Hoechst stain solution (Sigma-Aldrich). Cells treated with control (DMSO) or with 10 µM PKC412 were used for setting parameters.

Imaging and Analysis on an ArrayScan HCS System

Cell images were automatically obtained using an ArrayScan VTI HCS Reader (Cellomics, Pittsburgh, Pa., USA). Filter sets appropriate for detecting the two fluorophores were used, and a 20×0.4 numerical aperture microscope objective was used for imaging. The Compartmental Analysis BioApplication (Cellomics) was used to analyze the images after optimization of the application's protocol settings. For these analyses, the Compartmental Analysis used the Hoechst-labeled nuclei to identify individual cells, and the nucleus (Circle) and cytoplasmic area (Ring) of the cells were defined by parameter settings in the software. The GFP spots in the Ring region were defined and the spot numbers (Ring Spot Count) and spot intensity (Ring Spot Intensity) were quantified by the software.

RNA Isolation and Quantitative Real-Time RT-PCR Analysis

Total RNA from various cell lines was isolated using the TRIzol reagent (Invitrogen) and purified with the QIAGEN RNeasy Mini Kit, treated with DNase (DNase I, 30 U/µg total RNA; QIAGEN), and reverse transcribed using the SuperScript III First-Strand Synthesis System (Invitrogen). The levels of FGFR1, 2, 3, and 4 mRNA were quantified by real-time RT-PCR using SYBR Green PCR Master Mix and an ABI Prism 7900HT Sequence Detection System (Applied Biosystems). The primers used for RT-PCR were as follows:

```
FGFR1
Forward:
                                       (SEQ ID NO: 17)
5'-GAGATGGAGGTGCTTCACTTA-3'

Reverse:
                                       (SEQ ID NO: 18)
5'-TACAGGGGCGAGGTCATCA-3'

FGFR2
Forward:
                                       (SEQ ID NO: 19)
5'-ATGCTTGTACTGCCAGTAGGACTGT-3'

Reverse:
                                       (SEQ ID NO: 20)
5'-CTGACAAAATCTTCCGCACCAT-3'

FGFR3
Forward:
                                       (SEQ ID NO: 21)
5'-CCTCGGGAGATGACGAAGC-3'

Reverse:
                                       (SEQ ID NO: 22)
5'-CGGGCCGTGTCCAGTAAGG-3'

FGFR4
Forward:
                                       (SEQ ID NO: 23)
5'-TGCAGAATCTCACCTTGATTACA-3'
```

-continued

Reverse:
(SEQ ID NO: 24)
5'-GGGGTAACTGTGCCTATTCG-3' hGAPDH
Forward:
(SEQ ID NO: 25)
5'-TTCGCTCTCTGCTCCTCCTGT-3'

Reverse:
(SEQ ID NO: 26)
5'-GCCCAATACGACCAAATCCG-3'

Statistical Analysis

A two-tailed Student's t-test was used to test for differences between treatments. A p-value less than 0.05 was considered statistically significant (*p-value<0.05, p-value<0.01, *p-value<0.001).

Results

Figure 4:
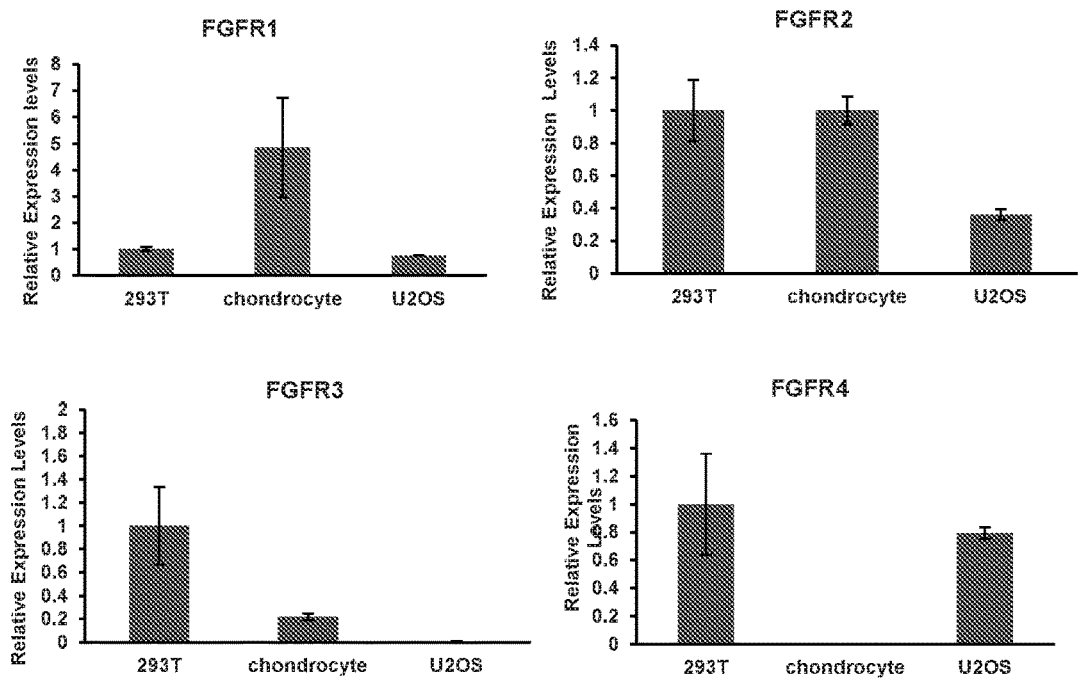
FIG. 4 shows bar graphs showing relative mRNA expression levels of FGFR1, FGFR2, FGFR3, and FGFR4 in embryonic kidney cells (293T), chondrocytes, and osteosarcoma cells (U205)

Establishment of a Stable Cell Line and Evaluation of the Subcellular Distribution of Effector-GFP Fusion Protein The expression levels of FGFR1-4 in 293T cells, chondrocytes, and U2OS human osteosarcoma cells were determined by quantitative RT-PCR as described above. Among the three cell types tested, only the U2OS cells endogenously express mRNA for FGFR1, 2 and 4, but not FGFR3. See FIG. 4. The U2OS cell line was chosen for developing a cell-based screening system for modulators of activated FGFR3 function. The SH2 domains of PLCγ and SH2-Bβ have been shown to interact with activated FGFR3 and transduce specific downstream signals. See Harada et al., Bone 41:273-281 and Kong et al., J. Biol. Chem. 277:15962-15970. RrGFP, RrGFP-PLCγ SH2 domain fusion protein, and RrGFP-SH2-Bβ SH2 domain fusion protein were transiently expressed in U2OS cells following the protocol set out above. The results showed that RrGFP signals were evenly distributed in U2OS cells. SH2(SH2-B)-RrGFP signals were distributed to both cytosol and nuclear compartments. By contrast, SH2(PLCγ)-RrGFP was localized to the plasma membrane, likely due to non-specific interactions of SH2(PLCγ)-RrGFP with endogenous FGFR1, 2, and 4, or with other receptor tyrosine kinases in U2OS cells.

The stable cell line homogeneously expressing SH2(SH2-B)-RrGFP was used for subsequent co-transfection with WT FGFR3 and various FGFR3-activating mutants. See FIGS. 5A and 5B. The expression of FGFR3 protein (WT and mutants) and SH2(SH2-B)-RrGFP protein in the stable cell lines was confirmed by Western blot analysis. Cells expressing WT FGFR3 and various activated FGFR3s exhibited a spotted, i.e., punctate, pattern of cytosolic SH2(SH2-B)-RrGFP fluorescence. No spots were observed in the SH2(SH2-B)-RrGFP cell line transfected with an empty expression vector. A portion of the internalized spot signals was co-localized with lysosomes, indicating that complexes of SH2(SH2B)-RrGFP and activated FGFR3 undergo internalization and degradation via the lysosomal pathway.

Cytosolic Fluorescent Spots Represent Internalized Complexes of Activated FGFR3 and SH2(SH2-B)-RrGFP The direct interaction of FGFR3 and SH2(SH2B)-RrGFP protein was examined by coimmunoprecipitation. The results showed that phosphorylated FGFR3 was detectable in cell lines containing various activated forms of FGFR3 and also showed that SH2(SH2B)-RrGFP protein was co-immunoprecipitated with FGFR3. The interaction between SH2(SH2B)-RrGFP and FGFR3 was further confirmed by immuno-colocalization, which showed that the majority of WT FGFR3 was located on the plasma membrane, whereas most activated FGFR3 was internalized and formed punctate signals in the cytosol. Complexes of activated FGFR3 and SH2(SH2B)-RrGFP, identified by co-localized staining, corresponded with the punctate SH2(SH2B)-RrGFP signals in the cytosol.

It is known that the SH2 domain interacts with activated FGFR3 through Tyr-724 and Tyr-760. See Harada et al., Bone 41:273-281. A Y373C (TDI FGF3) activated form of FGFR3 also carrying Y724F and Y760F mutations was tested for its interaction with SH2(SH2B)-RrGFP in transiently transfected cells. Punctate fluorescence signals were observed in the cytosol of SH2(SH2B)-RrGFP stable cells transiently expressing TDI FGFR3. By contrast, no punctate cytosolic fluorescence was observed in a SH2(SH2B)-RrGFP stable cell line transiently expressing Y724F/760E-substituted TDI FGFR3. Quantification of the punctate cytosolic fluorescence was performed as described in the next section and shown in FIG. 6C. The expression levels of FGFR3 between cells expressing TDI FGFR3 and those expressing Y724F/760E-TDI FGFR3 was the same. These results confirm that the punctate cytosolic florescence directly corresponds to internalized complexes of activated FGFR3 and SH2(SH2B)-RrGFP, and further confirm that FGFR3 residues Tyr-724 and Tyr-760 are important for FGFR3 interaction with SH2(SH2B)-RrGFP in cells.

Detection and Quantification of PKC412 Inhibition of FGFR3 Activation Using a High-Throughput Imaging System A cell imaging system suitable for high-throughput screening and quantification of FGFR3 inhibitor activity was established based on the RrGFP-expressing cells described above. First, the ability of this system to accurately quantify FGFR3 activation was tested using the tyrosine kinase inhibitor, PKC412. PKC412 is a small molecule tyrosine kinase inhibitor that has been shown to effectively inhibit cell growth in FGFR3-activating multiple myeloma cell lines by inhibiting tyrosine autophosphorylation of FGFR3. See Chen et al., Oncogene 24:8259-8267. As mentioned above, the TDI FGFR3 mutation leads to the most severe type of FGFR3 activation-related skeletal dysplasia. A stable cell line expressing both SH2(SH2B)-RrGFP and TDI FGFR3, which exhibited the highest level of internalized spot signals, was used in conjunction with PKC412 to optimize parameters for quantitative high-throughput cell-imaging application. Images of cells treated with dimethyl sulfoxide (DMSO; control) or PKC412 were acquired using an ArrayScan VIIHCS reader and analyzed with the associated Compartmental Analysis BioApplication. Punctate GFP signals in SH2(SH2B)-RrGFP and TDI FGFR3 expressing cells disappeared within 1 hour after treatment with PKC412 but not after treatment with DMSO. The two principle quantifiable features measured by the high-throughput imaging system, namely, ring spot counts and total ring spot intensity per cell, were evaluated for their ability to reflect the underlying biology. Ring spot counts and total ring spot intensity per cell were determined from a PKC412 dose-response assay and plotted as a percentage of the DMSO control response. The results are shown in FIG. 6A. The $IC_{50}$ values calculated from these two measured features were very similar, showing that either could be used to assess the pharmacological properties of inhibitors.

Ring spot counts quantified by the above method were used to compare the FGFR3 activation in cells stably expressing the SH2(SH2B)-RrGFP and WT FGFR3 or various activated FGFR3s treated with or without acidic fibroblast growth factor (aFGF) and heparin. The results are shown in FIG. 6B. The ring spot count was significantly increased with aFGF and heparin treatment in the cells expressing WT FGFR3. There was no significant difference in the ring spot count in cells expression various activated FGFR3 compared with or without aFGF and heparin treatment. The same quantitative method was also used to compare the SH2(SH2B)/GFP stable cells transiently expressing TD1 FGFR3 or Y724F/760F TD1 FGFR3 described above. See FIG. 6C. Note that the Y724F/760F TD1 FGFR3 does not interact with SH2 domains. Cells expressing SH2(SH2B)/GFP and the TDI FGFR3 mutant had a much higher ring spot count as compared to mock transfected cells. On the other hand, cells expressing SH2 (SH2B)/GFP and the Y724F/760F TDI FGFR3 showed litttle to no ring spots, confirming that the presence of ring spots correlates with the interaction between the TDI FGFR3 and the SH2 domain.

Example 3

Screening of Plant Extracts for FGFR3 Modulators Using the Cell-Based Translocation Assay System The cell-based translocation assay system described above was used to screen ethanol extracts obtained from 101 different plant species in order to identify agents capable of modulating FGFR3 activity.

Plant Extract Preparation

A plant extract library was created from 101 different plant species collected in Taiwan from the 57 taxonomic families shown below in Table 4.

TABLE 4

Plant families tested for FGFR3 activity modulators

| Family | number of species |
|---|---|
| ACANTHACEAE | 3 |
| ACERACEAE | 1 |
| AGAVACEAE | 2 |
| AMARANTHACEAE* | 2 |
| AQUIFOLIACEAE | 1 |
| ARACEAE | 2 |
| ARECACEAE | 1 |
| ARECACEAE | 1 |
| BIGNONIACEAE | 1 |
| BIXACEAE | 1 |
| BORAGINACEAE | 1 |
| CAPRIFOLIACEAE | 1 |
| CASUARINACEAE | 1 |
| CELASTRACEAE | 1 |
| CHLORANTHACEAE | 1 |
| COMPOSITAE | 3 |
| CORNCACEAE | 1 |
| CUPRESSACEAE | 1 |
| CYATHEACEAE | 1 |
| EBENACEAE | 1 |
| ELAEAGNACEAE | 1 |
| ELAEAGNACEAE | 1 |
| ERICACEAE | 1 |
| EUPHORBIACEAE | 7 |
| FAGACEAE | 8 |
| GESNERIACEAE | 1 |
| GRAMINEAE | 6 |
| GUTTIFERAE | 1 |
| HERNANDIACEAE | 1 |
| LAURACEAE | 4 |
| LEGUMINOSAE | 7 |
| LILIACEAE* | 1 |
| MAGNOLIACEAE | 1 |
| MALVACEAE | 1 |
| MELASTOMATACEAE | 1 |
| MORACEAE | 3 |
| MUSACEAE | 1 |
| MYRTACEAE | 3 |
| PALMAE | 3 |
| PASSIFLORACEAE | 1 |
| PINACEAE | 1 |
| PODOCARPACEAE | 1 |
| POLYGONACEAE | 1 |
| PTERIDACEAE | 1 |
| RANUNCULACEAE | 1 |
| ROSACEAE | 2 |
| RUBIACEAE | 1 |
| RUTACEAE | 2 |
| SALICACEAE | 1 |
| SAPOTACEAE* | 1 |
| SCROPHULARIACEAE | 1 |
| STERCULIACEAE | 2 |
| STYRACACEAE | 1 |
| TAXODIACEAE | 1 |
| THEACEAE | 2 |
| UMBELLIFERAE | 1 |
| ZINGIBERACEAE* | 1 |

*Positive hit identified in this family

Whole plants were dried, ground, and extracted with 95% ethanol. The ethanol extracts were dried by evaporation under reduced pressure in a rotary evaporator and were dissolved in DMSO to a concentration of 37 mg/ml.

Cell Proliferation Assay

Cell proliferation was determined by a colorimetric assay of cell viability based on the cleavage of the tetrazolium salt WST-1 (Roche) by mitochondrial dehydrogenases. Cells were grown in serum-free conditions for 24 h and then were seeded in 96-well plates at a density of 50,000 cells/well in RPMI. Cells were incubated with 1 nM aFGF and 50 µg/ml heparin and various doses of plant extracts in 200 µl RPMI at a final concentration of 1% DMSO. Plates were incubated for 72 h at 37° C., 5% $CO_2$. The WST-1 assay was performed according to the manufacturer's instructions. The absorbance of the formazan dye formed, which correlates with the number of metabolically active cells in the culture, was measured at 450 nm and 690 nm 1 h after adding the reagent. Each experimental condition was performed in triplicate.

Results

Identifying and Validating Plant Extract FGFR3 Modulating Activity

Figure 7A:
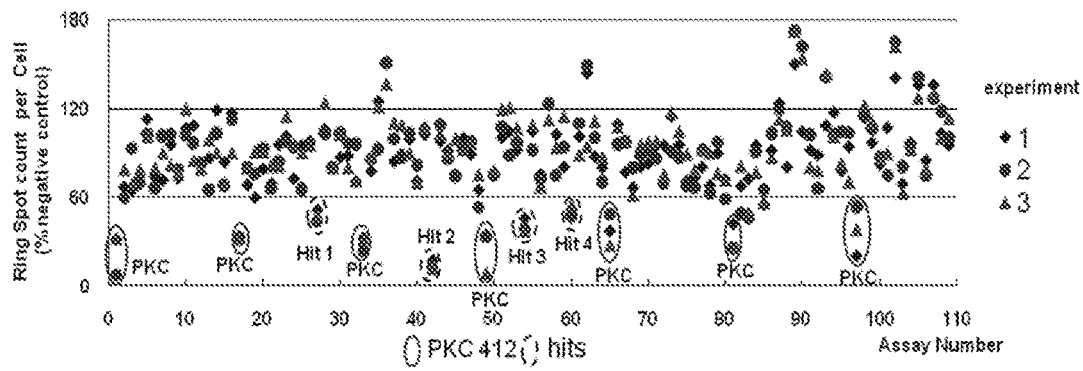
FIG. 7A shows ring spot count as a percentage of control for cells stably expressing SH2(SH2B)-RrGFP and TDI FGFR3 and treated with each of 101 plant extracts or with positive control PKC412. Samples indicated as hits had no more than 60% of the ring spot count of the negative control. The results of three experiments are plotted together.

The plant extracts described above were screened on cells expressing both SH2(SH2B)-RrGFP and TDI FGFR3 using the above-mentioned method to identify extracts containing an activity that inhibits FGFR3 activation. A screening result was considered to be positive (a "hit") if the measured ring spot counts per cell in cells treated with the extract was no more than 60% that in DMSO treated cells, i.e., controls. PKC412 was used as a positive control. The screening experiment was repeated 3 times. Based on the above criterion, 4 out of the 101 plant ethanol extracts tested were identified as hits in this preliminary screen ("hit1," "hit 2," "hit 3," and "hit 4"). In addition, some plant extracts were shown to enhance FGFR3 activation. The results are shown in FIG. 7A.

Figure 7B:
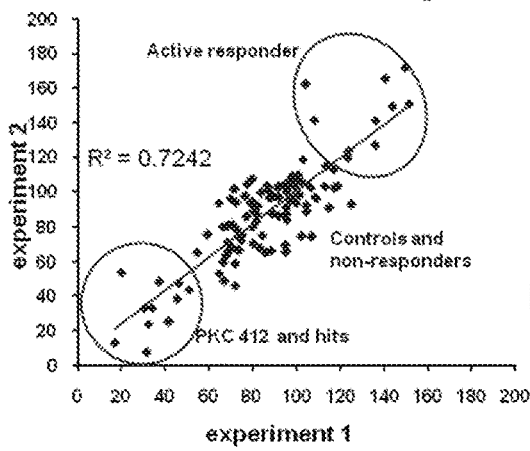
FIG. 7B is a linear regression analysis of the data shown in FIG. 7A.

To further confirm the reproducibility of hit results, a linear regression analysis of the results of screening experiments 1 and 2 was performed. The percentage of ring spot counts per cell compared to the DMSO control from these two experiments were plotted against each other for each plant extract and PKC412 treatment. The results are shown in FIG. 7B. The PKC412 treatments and the hits (circled in the lower-left corner of FIG. 7B) were clearly distinct from the DMSO control, non-responder, and activated-responder populations (circled in the upper-right corner of FIG. 7B).

Figure 7C:
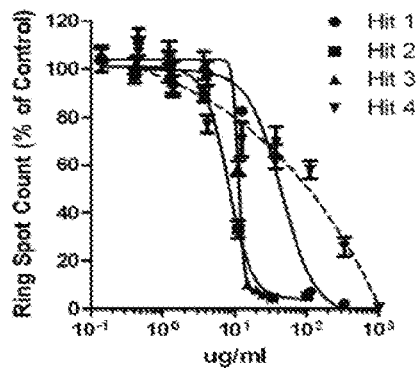
FIG. 7C is a plot of ring spot count as a percentage of control for cells stably expressing SH2(SH2B)-RrGFP and TDI FGFR3 and treated with the indicated doses of the positive hits (Hit 1, Hit 2, Hit 3, and Hit 4) shown in FIG. 7A.

A dose-response analysis of hit1, hit 2, hit 3, and hit 4 was performed by determining the percentage of ring spot counts per cell compared to DMSO control at different concentrations of plant extracts. The results are shown in FIG. 7C. Inhibition of FGFR3 activation by the four tested plant extracts was dose-dependent, providing additional confirmation of the screening results.

Figure 7D:
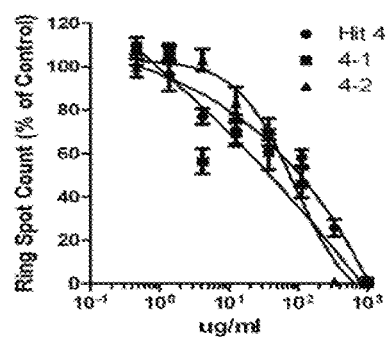
FIG. 7D is a plot of ring spot count as a percentage of control for cells stably expressing SH2(SH2B)-RrGFP and TDI FGFR3 treated with the indicated doses of Hit 4 and two extracts (4-1 and 4-2) from plants related to that from which Hit 4 arose.

Hit 4 arose from an ethanol extract of *Amaranthus viridis*. Ethanol extracts were also prepared from two closely related plant species. These two plant extracts, i.e., hit 4-1 (*Amaranthus spinosus) and hit 4-2 (*Amaranthus tricolor*), displayed a dose-dependent inhibition of FGFR3 activation similar to that of hit 4. See FIG. 7D.

Figure 7E:
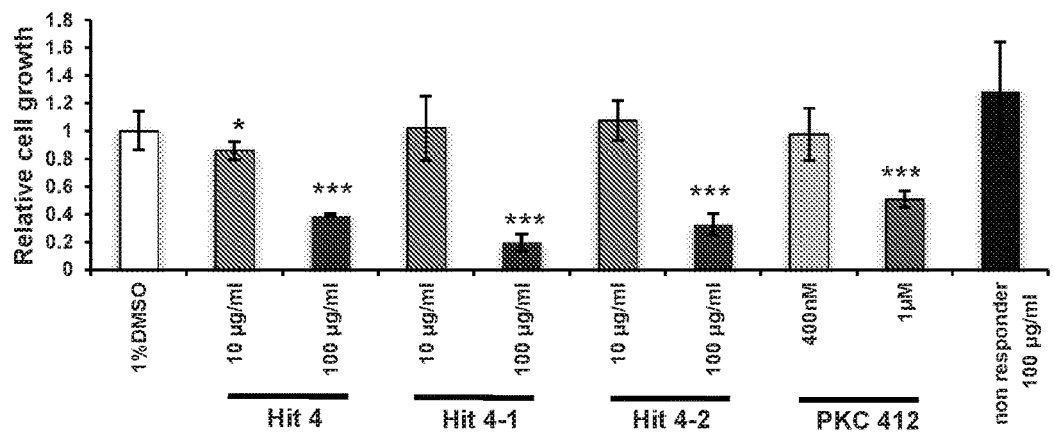
FIG. 7E is a bar graph showing relative growth of KMS-11 cells treated with vehicle (DMSO) or the indicated amounts of plant extracts Hit 4, 4-1, 4-2, and positive control PKC412. ***$p<0.001$.

Inhibition of Cell Proliferation and FGFR3 Signaling in FGFR3 Activated Primary Multiple Myeloma Cells The effects of hit 4, hit 4-1, and hit 4-2 were examined on the growth of human myeloma cell line KMS-11 ectopically expressing TDI FGFR3. KMS-11 cells were stimulated with aFGF/heparin and incubated with DMSO negative control, PKC412 positive control, or 10 µg/ml and 100 µg/ml doses of each tested plant extract. Cell growth was measured as described above. The results are shown in FIG. 7E. Inhibition of cell growth by hit 4, hit 4-1, and hit 4-2 at the 100 µg/ml dose was observed. A plant extract from a non-responder did not inhibit cell growth at the same dose.

The inhibition of KMS-11 cell growth by hit 4, hit 4-1, and hit 4-2 was correlated with the inhibition of FGFR3 phosphorylation and the inhibition of phosphorylation of possible FGFR3 signaling intermediates, including PLCγ, STAT5, PI3K, and ERK1/2, as determined by immunoblotting analysis of whole-cell lysates as described above in Example 2.

Example 4

Bioassay-Guided Plant Extract Fractionation and Purification of FGFR3 Activation Inhibitors Pheophorbide a and Pyropheophorbide a The cell-based translocation assay described above in Example 2 was used as a bioassay to identify plant extract fractions that inhibit FGF3R activity. Hit 4 discussed above is an extract from *A. viridis*. Fractions from this source were obtained and assayed for FGFR3 inhibitory activity as set forth, infra.

Preparation and Extraction of Plant Material

For a small-scale preparation, fresh *A. viridis* plants were collected, washed with water, dried in a 65° C. oven for 13 hours, and ground into a powder. The powder was extracted in 10 volumes of 95% ethanol with continuous stirring at room temperature for 16 hours. The ethanol extracts were filtered and concentrated in an evaporator.

Large-scale preparations of *A. viridis* extracts were prepared by the Industrial Technology Research Institute, Hsinchu, Taiwan. Briefly, fresh *A. viridis* plants (500 Kg) were collected, washed with water, dried in an oven at 65° C. for 13 hours, and chopped into small strips. The dried strips (47.3 Kg) were extracted by 95% ethanol reflux extraction for 24 h with intermittent stirring at 2 h intervals and repeated once. The extract was concentrated via an evaporator to a final solid content of 6.43% in 25.7 L of ethanol. The extract was stored at 4° C. prior to use.

Partition and Fractionation of the Ethanol Extract of *A. Viridis*.

Figure 8:
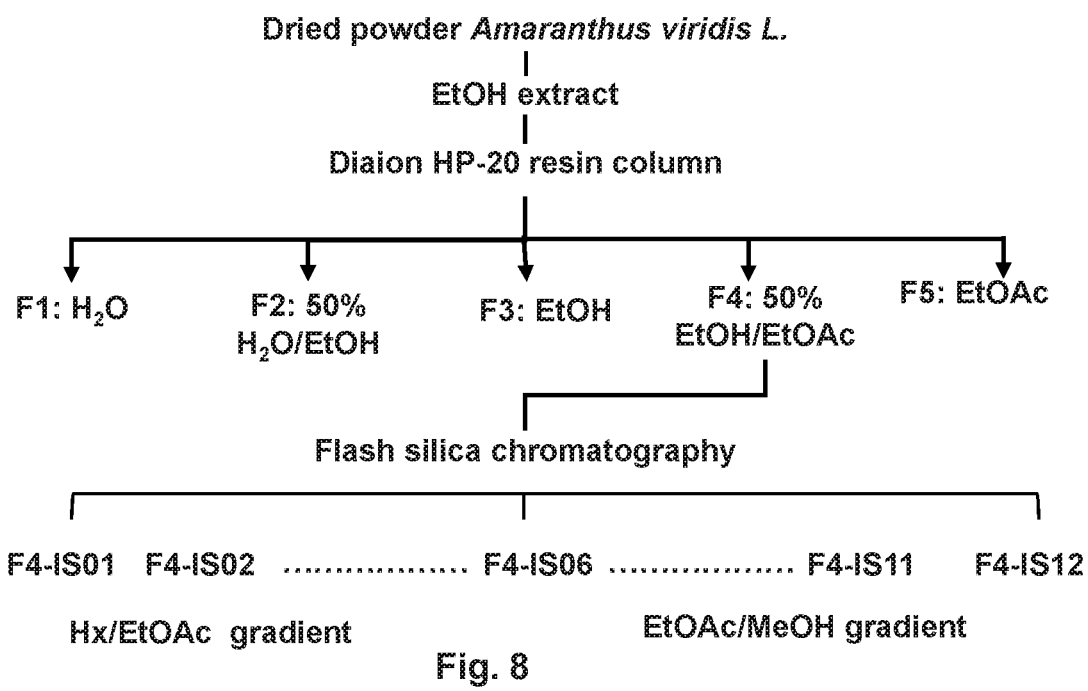
FIG. 8 is a flow-chart of a purification scheme for isolating active fractions from an ethanol extract of *Amaranthus viridis*.

The crude ethanol extract described above was further fractionated as illustrated in FIG. 8. The ethanol extract was loaded onto a Diaion HP-20 column (80×240 mm) and eluted stepwise with 100% $H_2O$ (fraction 1; F1), 50% v/v ethanol in $H_2O$ (EtOH/$H_2O$ fraction 2; F2), 100% ethanol (EtOH fraction 3; F3), 50% (v/v) ethanol in ethyl acetate (EtOH/EtOAc fraction 4; F4), and 100% ethyl acetate (EtOAc fraction 5; F5). Each fraction was concentrated in an evaporator and stored at −20° C. until use.

The F4 fraction was subjected to column chromatography to separate the extract into 107 fractions. Silica gel was used as the stationary phase while solvent systems of gradually increasing polarity, namely, hexane in ethyl acetate and ethyl acetate in methanol, were used as the mobile phase. The eluted fractions were collected and concentrated by evaporator. The fractions were stored at −20° C.

High-Performance Liquid Chromatography Analysis

Plant fractions were analyzed by high-performance liquid chromatography (HPLC). The fractions were added to 50% HPLC-grade methanol (MeOH) to a concentration of 10 mg/mL. Samples were separated using HPLC system (SpectraSYSTEM AS) equipped with a SpectraSYSTEM P1000 pump, a Thermo UV6000LP. Reverse-phase chromatographic analysis was carried out in isocratic conditions using a C-18 reverse phase column (250×4.6 mm i.d., particle size 5 µm, Luna 5µ C-18(2); phenomenex, Torrance, Calif., USA) at 25° C. Running conditions were as follows: injection volume, 5 µl; mobile phase, methanol: 0.4% acetic acid (80:20 v/v); flow rate, 1 ml/min; detection at 290 nm. Samples were filtered through an ultrafiltration membrane (pore size 0.45 µm; E-Merck, Darmstadt, Germany) prior to injection in the sample loop.

UV-Visible Spectroscopy

Spectral studies were carried out by spectrophotometry (Perkin-Elmer). All solvents used for spectral studies were of analytical grade. Thee milliliter quartz cuvettes were used for all studies.

Analytical Thin Layer Chromatography and Pooling of Fractions

Each of the 107 fractions of F4 obtained from silica gel chromatography was spotted on aluminum thin layer chromatography (TLC) plates coated with silica gel F254. The spotted TLC plate was placed in a small chromatographic tank to separate the fractions based on their relative mobilities in solvent systems. The solvent system used for fractions 1-72 was ethanol-hexane 25:75 (v/v) and for fractions 73-107 was acetone-methanol 9:1 (v/v). Chromatography patterns were visualized under ultra-violet light. The 107 fractions were combined into 12 fractions based on the similarity of their TLC patterns.

High-Content Cell-Based Translocation Assay

*A. viridis* extract fractions were analyzed using the high-content cell-based translocation assay described above in Example 2.

Cell Proliferation Assay

Fractions were analyzed for their ability to inhibit the FGFR3 activity-dependent growth of human myeloma cell line KMS-11 as described above in Example 3.

Data Analysis

Dose-response curves and for FGFR3 inhibition were analyzed using Prism 5.02 (GraphPad). The statistical significance of differences between two groups of data was analyzed by paired t test and P values<0.05 were considered significant.

Results

Identification of Bioactive Fractions from *A. Viridis* that Inhibit FGFR3 Activation As mentioned above, the bioactive extract that inhibits FGFR3 activation and designated as hit 4 is an ethanol extract of *A. viridis*. To further characterize the bioactive fractions and compounds from the ethanol extract of *A. viridis*, additional fractionation was carried out through bioassay-guided isolation. Five fractions, i.e., F1-F5, of an *A. viridis* ethanol extract were obtained from two independently isolated ethanol extracts of *A. viridis* following the fractionation scheme shown in FIG. 8. The recovery rate of the fractions is shown below in Table 5. One extract (A-E01) was a small-scale extract and the other (A-E02) a large-scale extract as set forth, supra.

TABLE 5

The recovery rate of the partitioned fractions.

| Fractions | | Recovery (%) A-E01 | Recovery rate (%) A-E02 |
|---|---|---|---|
| A-F1 | 100% H$_2$O | 50.59 | 50.57 |
| A-F2 | 50% H$_2$O/EtOH[a] | 26.25 | 7.71 |
| A-F3 | 100% EtOH | 12.54 | 8.43 |
| A-F4 | 50% EtOH/EA | 23.80 | 24.76 |
| A-F5 | 100% EA | 0.52 | 1.10 |
| Total | | 112.98 | 92.57 |

[a]EtOH: ethanol; EA: Ethyl Acetate

Figure 9:
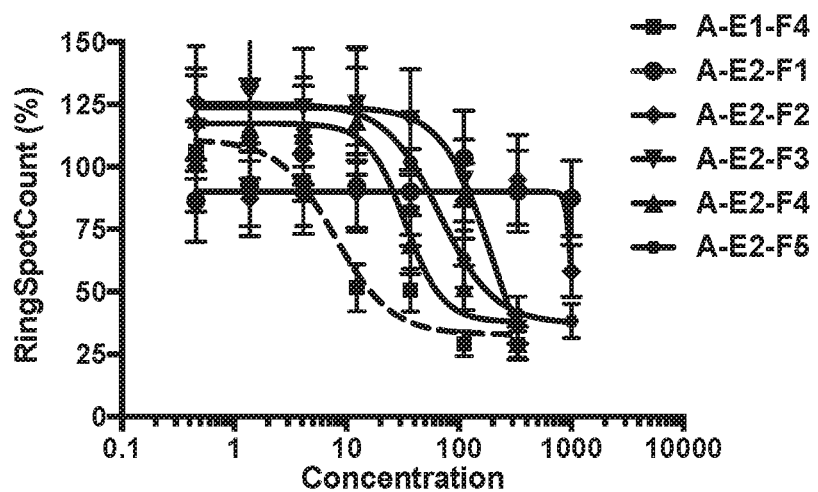
FIG. 9 is a plot of ring spot count as a percentage of control for cells stably expressing SH2(SH2B)-RrGFP and TDI FGFR3 treated with the indicated doses of *A. viridis* fractions (F1-F4) isolated according to the flow-chart shown in FIG. 8.

The inhibitory activity of each *A. viridis* fraction on FGFR3 activation was analyzed by the cell-based translocation assay system described above. The results are shown in FIG. 9. Among the five tested fractions, fractions F3, F4, and F5 showed inhibition of FGFR3 activation, with fraction F4 having the lowest 50% inhibitory concentration (IC$_{50}$=3.63 µg/ml) of FGFR3 activation as compared with the other tested fractions As mentioned above, two independent *A. viridis* ethanol extracts were isolated. The second, large-scale extract was isolated from a batch of *A. viridis* plants collected from different location in different seasons. The first batch was collected from Taipei, Taiwan in the Spring and the second batch was collected from Tainan, Taiwan, in the Summer. The F4 fractions obtained from the two different *A. viridis* preparations, namely, A-E1-F4 and A-E2-F4, showed similar patterns in HPLC, UV, CAD, and MS analysis. Yet, the activity of the F4 fraction from the large-scale preparation (A-E2-F4) had lower FGFR3 inhibitory activity as compared to the F4 fraction obtained from the small-scale preparation (A-E1-F4) (E1-F4, IC$_{50}$=7.918 µg/ml; E2-F4, IC$_{50}$=33.31 µg/ml).

The F4 fraction obtained from the large-scale *A. viridis* preparation was further fractionated by phase chromatography on silica gel into 107 fractions, and each of these fractions was analyzed by TLC. The 107 fractions were pooled based on the similarity of TLC pattern into 12 fractions (F4-IS1 to F4-IS12). The recovery rate of the 12 fractions is shown below in Table 6 below.

TABLE 6

Recovery rates of 12 fractions from A-E2-F4

| A-E2-F4 | Recovery rate (%) |
|---|---|
| F4-IS01 | 1.58 |
| F4-IS02 | 21.84 |
| F4-IS03 | 18.71 |
| F4-IS04 | 4.91 |
| F4-IS05 | 4.87 |
| F4-IS06 | 9.33 |
| F4-IS07 | 4.53 |
| F4-IS08 | 7.37 |
| F4-IS09 | 1.10 |
| F4-IS10 | 5.92 |
| F4-IS11 | 3.25 |
| F4-IS12 | 4.46 |
| Total | 87.87 |

Figure 10A:
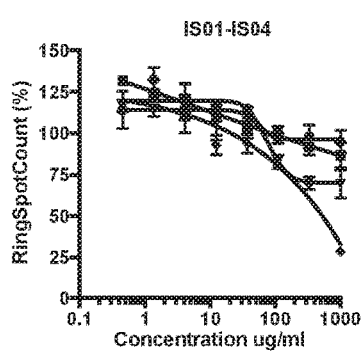
FIG. 10A is a plot of ring spot count as a percentage of control for cells stably expressing SH2(SH2B)-RrGFP and TDI FGFR3 treated with the indicated doses of *A. viridis* sub-fractions 1-4 (IS01-IS04) of fraction F4.
Figure 10B:
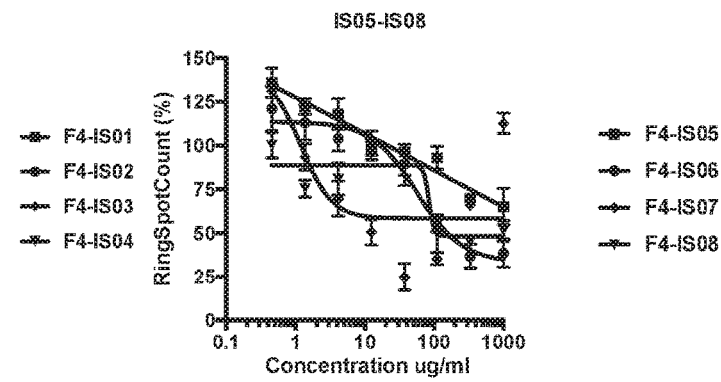
FIG. 10B is a plot of ring spot count as a percentage of control for cells stably expressing SH2(SH2B)-RrGFP and TDI FGFR3 treated with the indicated doses of *A. viridis* sub-fractions 5-8 (IS05-IS08) of fraction F4.
Figure 10C:
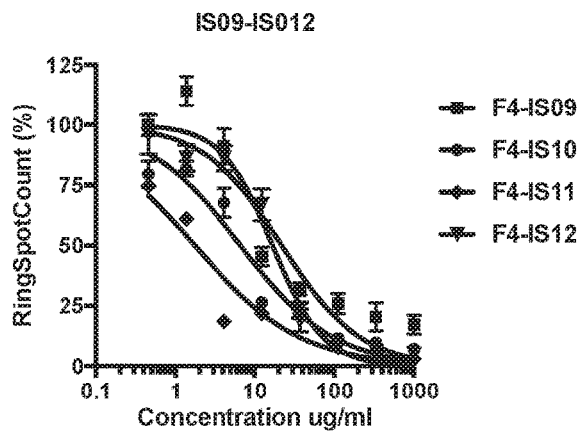
FIG. 10C is a plot of ring spot count as a percentage of control for cells stably expressing SH2(SH2B)-RrGFP and TDI FGFR3 treated with the indicated doses of *A. viridis* sub-fractions 9-12 (IS09-IS12) of fraction F4.

The FGFR3 inhibitory activities of F4-IS01 to F4-IS12 were analyzed by the cell-based translocation assay system. The results are shown in FIGS. 10A-10C. The F4-IS10 and F4-IS11 fractions showed the highest inhibition of FGFR3 activation, with an IC$_{50}$ of 6.605 µg/ml and 1.747 µg/ml, respectively. See FIG. 10C.

The Active Fractions Inhibit Growth of KMS-11 Cells

The effects of active fractions F4-IS-10 and F4-IS-11 on the growth of human myeloma cell line KMS-11, whose growth depends upon ectopic expression of Y373C FGFR3. Both F4-IS-10 and F4-IS-11 inhibited proliferation of KMS-11 cells, thus confirming the results of the cell-based translocation assay.

Isolation and Structural Elucidation of Active Compounds

To further purify the active fractions, a large scale ethanol extract of *A. viridis* was prepared and sub-fractionated using solvent partition with (i) 25% hexane in ethyl acetate, (ii) 50% hexane in ethyl acetate, (iii) 70% hexane in ethyl acetate, (iv) ethyl acetate, and (v) 50% methanol on acetone. Twenty one fractions were obtained from 64.81 g of starting material, as shown below in Table. 7.

TABLE 7

Ethanol extraction and solvent partition of *A. viridis* ethanol extract.

| Fraction X-EA-C | Solvent | Sample Weight (g) |
|---|---|---|
| 1 | 25% HX/EA | 0.0643 |
| 2 | | 0.3159 |
| 3 | | 0.2728 |
| 4 | | 0.5885 |
| 5 | | 0.6119 |
| 6 | 50% HX/EA | 0.7903 |
| 7 | | 2.3039 |
| 8 | | 2.7558 |
| 9 | | 1.4272 |
| 10 | | 1.3155 |
| 11 | 70% HX/EA | 1.5326 |
| 12 | | 1.9887 |
| 13 | | 0.5848 |
| 14 | | 0.4665 |
| 15 | | 0.5230 |
| 16 | EA | 0.4900 |
| 17 | | 1.1514 |
| 18 | | 0.9896 |
| 19 | | 0.7821 |
| 20 | | 0.6944 |
| 21 | 50% MeOH/ Acetone | 13.8038 2.8894 |
| Total weight | | 36.3424 |
| Total Sample (g) | 64.81 | Yield 56.08% |

HX, hexane;
EA, ethyl acetate;
MeOH, methanol.

Each fraction was tested for the ability to inhibit FGFR3 activity using the cell-based assay system. The results showed that fraction X-EA-C11 and 12 had the highest inhibitory activity against FGFR3 activation. These two fractions were subjected to further purification by reverse phase chromatography to yield 110 fractions from X-EA-C11 and 117 fractions from X-EA-C12. Each of these fractions was tested for its ability to inhibit FGFR3 activation in the cell-based assay. Fractions exhibiting greater than 60% inhibition activity were subjected to further dose responses assay. Fraction 1987-N-100 was the most potent inhibitor of FGFR3 activation and was chosen for further purification.

Fraction 1987-N-100 was sub-fractionated by reverse-phase chromatography into 8 fractions. All 8 fractions were tested in the cell-based assay for inhibition of FGFR3 activation. Among them, fractions C2156-N3 and C2156-N5 had the highest FGFR3 inhibitory activity. These two fractions were further analyzed using high resolution MA, MS/MS, IR, and NMR. The NMR data were used to identified the main chemical constituents of the C2156-N3 and C2156-N5 fractions as pheophorbide a ("Pa") and Pyropheophorbide a ("PyroPa"), respectively.

Pheophorbide a and Pyropheophorbide a Inhibit FGFR3 Activation

The abilities of Pa and PyroPa to inhibit the FGFR3 activation were determined in the cell-based translocation assay system. The results showed that both Pa and PyroPa inhibit FGFR3 activation. Pa was also tested in the KMS11 cell proliferation assay. It inhibited FGFR3-dependent cell proliferation of these cells.

Derivatives of Pa Inhibit FGFR3 Activation

Figure 11A:
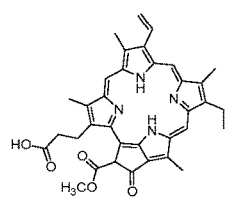
FIG. 11A shows the structure of pheophorbide derivatives HCl-N-Pa and Na-Pa.
Figure 11A:
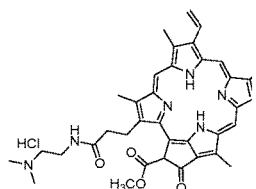
Figure 11A:
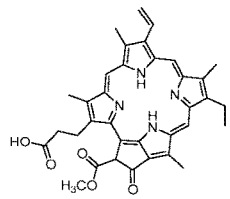
Figure 11B:
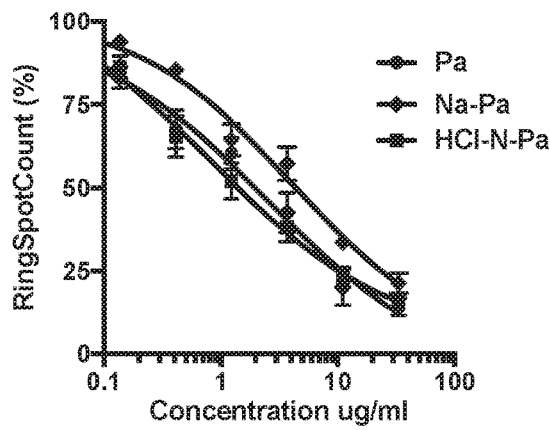
FIG. 11B is a plot of ring spot count as a percentage of control for cells stably expressing SH2(SH2B)-RrGFP and TDI FGFR3 treated with the indicated doses of HCl-N-Pa, Pa, or Na-Pa.

Derivatives of Pa were prepared with the goal of enhancing potency and solubility. Two such derivatives, namely, HCl-N-pheophorbide a (HCl-N-Pa) and Na-pheophorbide a (NA-Pa) are shown in FIG. 11A. Both derivatives have enhanced solubility, as compared to Pa, and have comparable FGFR3 inhibition activities, as assessed by the cell-based assay. See FIG. 11B.

Figure 12:
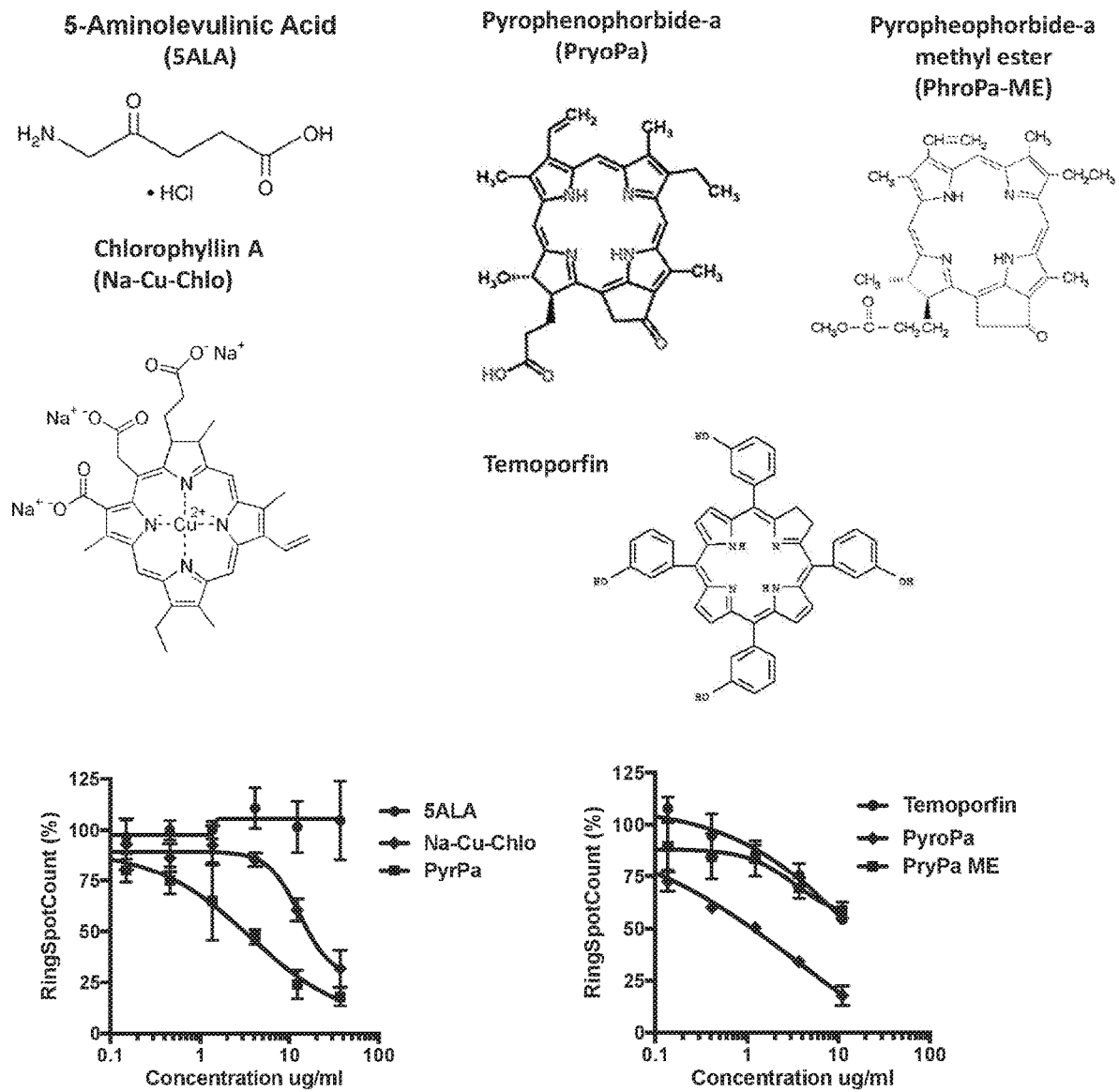
FIG. 12 shows the structures of photosensitizers (top) tested for their ability to inhibit FGFR3 activity and plots (bottom) of ring spot counts as a percentage of control for cells stably expressing SH2(SH2B)-RrGFP and TDI FGFR3 treated with the indicated doses of photosensitizers or PyroPa.
Figure 13A:
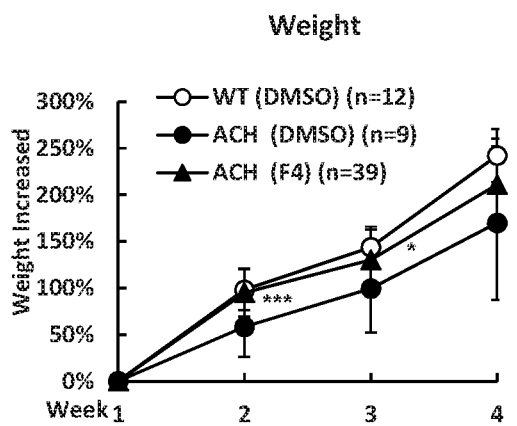
FIG. 13A is a plot of weight increase over time, expressed as percentage of control, in 7-day old wild-type (WT) or homozygous ACH (FGFR3 ACH/ACH) mice treated as indicated with DMSO or with active fraction 4 (F4) from *A. viridis*.
Figure 13B:
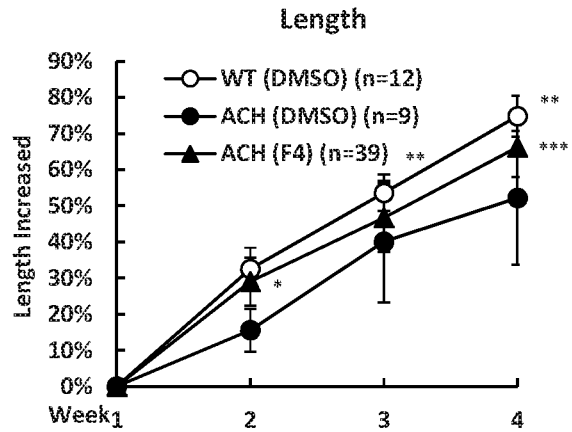
FIG. 13B is a plot of length increase over time, expressed as percentage of control. Mice and samples are as indicated in the legend.
Figure 13C:
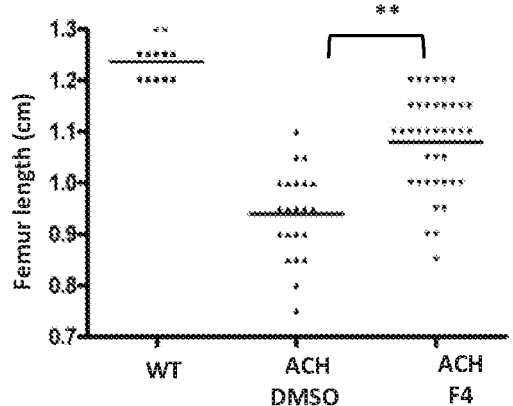
FIG. 13C is a plot of femur length over time. Mice and samples are as indicated in the legend to FIG. 13A.
Figure 13D:
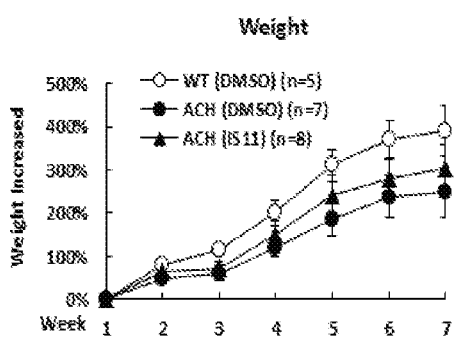
FIG. 13D is a plot of weight increase over time, expressed as percentage of control, in 7-day old WT or FGFR3 ACH/ACH mice treated with DMSO or with active sub-fraction IS11 from *A. viridis*.
Figure 13E:
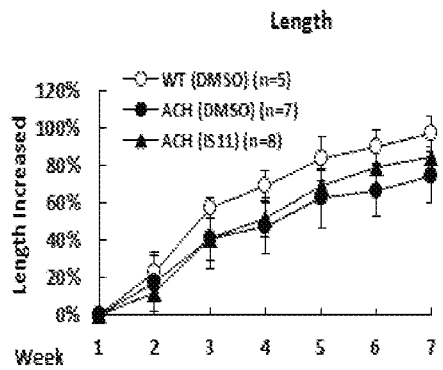
FIG. 13E is a plot of length increase over time, expressed as percentage of control. Mice and samples are as indicated.
Figure 13F:
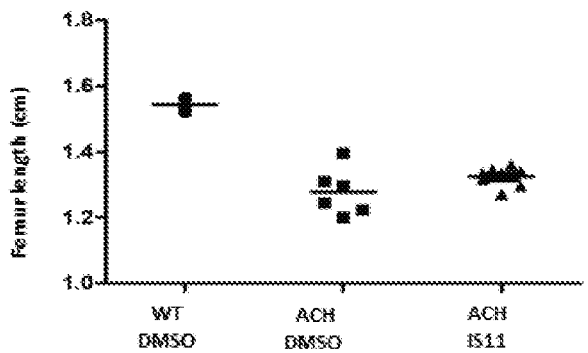
FIG. 13F is a plot of femur length over time. Mice and samples are as indicated in the legend to FIG. 13D.

Pa has been used as a chlorine-based photosensitizer and exhibits antitumor activity. The ability of four other photosensitizers, three structurally related to Pa and one distinct from it, were tested for FGFR3 inhibition activity. The results are shown in FIG. 12. The data demonstrated that the three compounds related in structure to Pa, namely, chlorophyllin A, temoporfin, and pyropheophorbide-a methyl ester, had FGFR3 inhibition activity, and the unrelated compound 5-aminolevulinic acid did not. Of note, the FGFR3 inhibition activity of PyroPa was stronger than any of the tested photosensitizers.

Example 5

In Vivo Inhibition of FGFR3 Activation with Plant Extracts and Pure Compounds for Treating Achondroplasia Plant extract fractions F4 and F4-IS11 and purified Pa described above in Example 4 were tested for their effect on achondroplasia in vivo.

Treatment of Achondroplasia Mice

Mice were housed in a temperature- and humidity-controlled room with a 12-hour light/12-hour dark cycle under specific pathogen-free conditions. All animal protocols were approved by the institutional animal care and use committee, Academia Sinica, Taiwan. The achondroplasia (FGFR3$^{ACH/ACH}$) mice are described above in Example 1.

FGFR3$^{ACH/ACH}$ mice beginning at 7 days of age were treated once-daily with 0.2 mg/g/mouse plant active fractions F4 and F4-IS11 by gavage in 200 μl PBS for 4 or 7 weeks. Control wild type littermates (WT) and FGFR3$^{ACH/ACH}$ mice were treated with vehicle control. In additional studies, mice were treated with 0.09 mg/g/mouse purified Pa or vehicle control in a similar manner. Body weight and body length were measured weekly.

Skeletal Analysis

Skeletons were analyzed by two-dimensional imaging (Skyscan 1076 system, Bruker, Brussels, Belgium) as described above.

The Active Fractions Improve the Clinical Phenotypes and Skeletal Development of ACH Mice The clinical efficacy of the active fractions, namely, F4 and F4-IS11, in attenuating the dwarfism phenotypes of FGFR3$^{ACH/ACH}$ mice was assessed. The results are shown in FIGS. 13A-F. As expected, FGFR3$^{ACH/ACH}$ mice had lower body weights, body length, and shorter femur lengths, as compared to their wild-type littermates (WT). See FIGS. 13A-13F, compare FGFR3 hACH/hACH(DMSO) to WT(DMSO). Seven-day-old FGFR3$^{ACH/ACH}$ mice treated with F4 and F4-IS11 demonstrated increased body weight, body length, and femur length, as compared to vehicle-treated FGFR3$^{ACH/ACH}$ mice. See FIGS. 13A-C and FIGS. 13D-F, respectively.

The improved skeletal development of active-fraction-treated FGFR3$^{ACH/ACH}$ mice compared to vehicle treated FGFR3$^{ACH/ACH}$ mice was also analyzed by two-dimensional micro-CT. F4-IS11 treated FGFR3$^{ACH/ACH}$ mice presented an attenuated dwarfism phenotype that included flattening of the rounded skull, elongation of the short snout, correction of the protruding lower incisors, and improvement of kyphosis.

Figure 14:
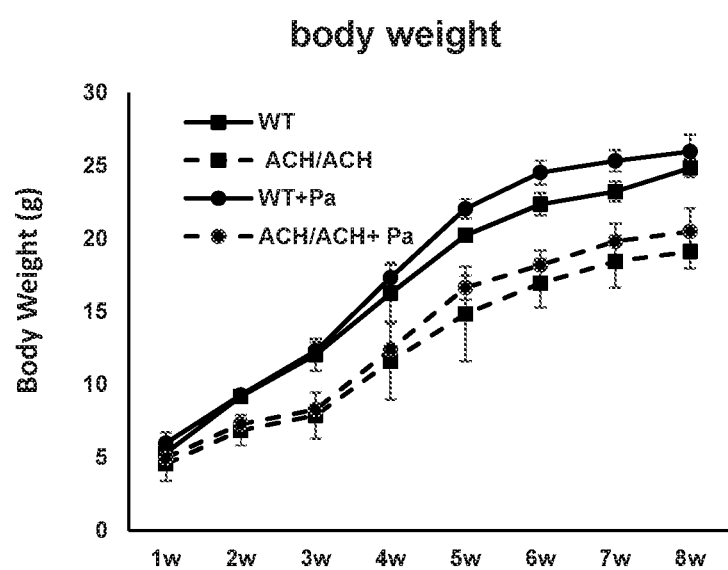

As mentioned above, Pa was identified as an active compound in the *A. viridis* extract by means of the method set forth above in Example 4. WT and FGFR3$^{ACH}$ mice at 7 days of age were treated with vehicle (DMSO) or with 0.09 mg/g/mouse Pa for 7 weeks. The body weight of treated mice was measured weekly. The results are shown in FIG. 14. Both WT mice and FGFR3$^{ACH}$ mice treated with Pa displayed increased body weight, as compared to mice treated with DMSO.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the described embodiments, and without departing from the spirit and scope thereof, can make various changes and modifications of the embodiments to adapt it to various usages and conditions. Thus, other embodiments are also within the claims.

The invention claimed is:

1. A knock-in mouse, comprising
one or two heterologous genomic nucleic acids, wherein the one or two heterologous genomic nucleic acids each replaces a coding region of an endogenous mouse Fibroblast growth factor receptor 3 (Fgfr3) gene and is operably linked to an endogenous mouse Fgfr3 promoter, the one or two heterologous genomic nucleic acids, individually, encoding a human wild-type FGFR3 or a human FGFR3(G380R) mutant, under the full control of the endogenous mouse Fgfr3 promoter region and including exon 1, intron 1, exon 2 and 5' and 3' untranslated regions of the mouse Fgfr3 gene, wherein at least one of the heterologous genomic nucleic acid encodes the human FGFR3(G380R) mutant, whereby the knock-in mouse has an externally dominant short stature, rounded head, short snout, and humpback, and skeletal abnormalities including rhizomelic dwarfism, rounded skull, and curvature of the cervical and upper thoracic vertebrae, relative to a knock-in homozygous or heterozygous mouse counterpart comprising the human wild-type FGFR3 and not the human FGFR3(G380R) mutant.

2. The knock-in mouse of claim 1, wherein the mouse contains both of the heterologous genomic nucleic acids.

3. The knock-in mouse of claim 2, wherein each of the heterologous genomic nucleic acids encodes the FGFR3 (G380R) mutant.

4. A knock-in mouse, which is selected from the group consisting of
(i) a knock-in mouse comprising one heterologous genomic nucleic acid which replaces a coding region of an endogenous mouse Fgfr3 gene and is operably linked to an endogenous mouse Fgfr3 promoter, said heterologous genomic nucleic acid encoding a human FGFR3(G380R) mutant under the full control of the endogenous mouse Fgfr3 promoter region and including exon 1, intron 1, exon 2 and 5' and 3' untranslated regions of the mouse Fgfr3 gene,
(ii) a knock-in mouse comprising two heterologous genomic nucleic acids each of which replaces a coding region of an endogenous mouse Fgfr3 gene and is operably linked to an endogenous mouse Fgfr3 promoter, one of said heterologous genomic nucleic acids encoding a human wild-type FGFR3 and the other encoding a human FGFR3(G380R) mutant, under the full control of the endogenous mouse Fgfr3 promoter region and including exon 1, intron 1, exon 2 and 5' and 3' untranslated regions of the mouse Fgfr3 gene,
(iii) a knock-in mouse comprising two heterologous genomic nucleic acids each of which replaces a coding region of an endogenous mouse Fgfr3 gene and is operably linked to an endogenous mouse Fgfr3 promoter, both of said heterologous genomic nucleic acids encoding a human FGFR3(G380R) mutant under the full control of the endogenous mouse Fgfr3 promoter region and including exon 1, intron 1, exon 2 and 5' and 3' untranslated regions of the mouse Fgfr3 gene,
wherein the knock-in mouse has an externally dominant short stature, rounded head, short snout, and humpback, and skeletal abnormalities including rhizomelic dwarfism, rounded skull, and curvature of the cervical and upper thoracic vertebrae, relative to a knock-in homozygous or heterozygous mouse counterpart comprising the human wild-type FGFR3 and not the human FGFR3(G380R) mutant.

* * * * *

SEQUENCE LISTING

```
<160> NUMBER OF SEQ ID NOS: 29

<210> SEQ ID NO 1
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 1

Gly Glu Pro Glu Gly Gly Glu Gly Asp Gln Pro Leu Ser Gly Tyr Pro
1               5                   10                  15

Trp Phe His Gly Met Leu Ser Arg Leu Lys Ala Ala Gln Leu Val Leu
            20                  25                  30
```

Thr Gly Gly Thr Gly Ser His Gly Val Phe Leu Val Arg Gln Ser Glu
        35                  40                  45

Thr Arg Arg Gly Glu Tyr Val Leu Thr Phe Asn Phe Gln Gly Lys Ala
 50                  55                  60

Lys His Leu Arg Leu Ser Leu Asn Glu Glu Gly Gln Cys Arg Val Gln
 65                  70                  75                  80

His Leu Trp Phe Gln Ser Ile Phe Asp Met Leu Glu His Phe Arg Val
                 85                  90                  95

His Pro Ile Pro Leu Glu Ser Gly Gly Ser Ser Asp Val Val Leu Val
                100                 105                 110

Ser Tyr Val Pro Ser Ser Gln Arg Gln Gln
                115                 120

<210> SEQ ID NO 2
<211> LENGTH: 233
<212> TYPE: PRT
<213> ORGANISM: Artificial Sequence
<220> FEATURE:
<223> OTHER INFORMATION: Synthetic polypeptide

<400> SEQUENCE: 2

Val Ser Ser Ser Thr Glu Leu His Ser Asn Glu Lys Trp Phe His Gly
 1               5                  10                  15

Lys Leu Gly Ala Gly Arg Asp Gly Arg His Ile Ala Glu Arg Leu Leu
                 20                  25                  30

Thr Glu Tyr Cys Ile Glu Thr Gly Ala Pro Asp Gly Ser Phe Leu Val
                 35                  40                  45

Arg Glu Ser Glu Thr Phe Val Gly Asp Tyr Thr Leu Ser Phe Trp Arg
 50                  55                  60

Asn Gly Lys Val Gln His Cys Arg Ile His Ser Arg Gln Asp Ala Gly
 65                  70                  75                  80

Thr Pro Lys Phe Phe Leu Thr Asp Asn Leu Val Phe Asp Ser Leu Tyr
                 85                  90                  95

Asp Leu Ile Thr His Tyr Gln Gln Val Pro Leu Arg Cys Asn Glu Phe
                100                 105                 110

Glu Met Arg Leu Ser Glu Pro Val Pro Gln Thr Asn Ala His Glu Ser
            115                 120                 125

Lys Glu Trp Tyr His Ala Ser Leu Thr Arg Ala Gln Ala Glu His Met
        130                 135                 140

Leu Met Arg Val Pro Arg Asp Gly Ala Phe Leu Val Arg Lys Arg Asn
145                 150                 155                 160

Glu Pro Asn Ser Tyr Ala Ile Ser Phe Arg Ala Glu Gly Lys Ile Lys
                165                 170                 175

His Cys Arg Val Gln Gln Glu Gly Gln Thr Val Met Leu Gly Asn Ser
            180                 185                 190

Glu Phe Asp Ser Leu Val Asp Leu Ile Ser Tyr Tyr Glu Lys His Pro
        195                 200                 205

Leu Tyr Arg Lys Met Lys Leu Arg Tyr Pro Ile Asn Glu Glu Ala Leu
    210                 215                 220

Glu Lys Ile Gly Thr Ala Glu Pro Asp
225                 230

<210> SEQ ID NO 3
<211> LENGTH: 17
<212> TYPE: DNA
<213> ORGANISM: Artificial Sequence

```
<220> FEATURE:
<223> OTHER INFORMATION: Synthetic oligonucleotide

<400> SEQUENCE: 3
tgcggtgcct tcacaga                                                  17

<210> SEQ ID NO 4
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 4
acttggacct ctccgtg                                                  17

<210> SEQ ID NO 5
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 5
gctgaggaca caggtgtg                                                 18

<210> SEQ ID NO 6
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 6
cactccctcc atctcctg                                                 18

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
ccagaacatc atccctgcat                                               20

<210> SEQ ID NO 8
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 8
gttcagctct gggatgacct t                                             21

<210> SEQ ID NO 9
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 9
cgaggcgggc agtgtgtgtg caggcat                                       27
```

```
<210> SEQ ID NO 10
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 10
atgcctgcac acacactgcc cgcctcg                                           27

<210> SEQ ID NO 11
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 11
gcatcctcag ctacagggtg ggcttcttc                                         29

<210> SEQ ID NO 12
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 12
gaagaagccc accctgtagc tgaggatgc                                         29

<210> SEQ ID NO 13
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 13
ggaaacacaa aaacatcatc aaactgctgg gcgcc                                  35

<210> SEQ ID NO 14
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 14
ggcgcccagc agtttgatga tgttttttgtg tttcc                                 35

<210> SEQ ID NO 15
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 15
cctcgactac tacaaggaga caaccaacgg ccg                                    33

<210> SEQ ID NO 16
<211> LENGTH: 33
<212> TYPE: DNA
<213> ORGANISM: Artificial Sequence
<220> FEATURE:
<223> OTHER INFORMATION: Synthetic oligonucleotide
```

<400> SEQUENCE: 16
cggccgttgg ttgtctcctt gtagtagtcg agg                                          33

<210> SEQ ID NO 17
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 17
gagatggagg tgcttcactt a                                                       21

<210> SEQ ID NO 18
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 18
tacaggggcg aggtcatca                                                          19

<210> SEQ ID NO 19
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 19
atgcttgtac tgccagtagg actgt                                                   25

<210> SEQ ID NO 20
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 20
ctgacaaaat cttccgcacc at                                                      22

<210> SEQ ID NO 21
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 21
cctcgggaga tgacgaagc                                                          19

<210> SEQ ID NO 22
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 22
cgggccgtgt ccagtaagg                                                          19

<210> SEQ ID NO 23

```
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 23
tgcagaatct caccttgatt aca                                          23

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
ggggtaactg tgcctattcg                                              20

<210> SEQ ID NO 25
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 25
ttcgctctct gctcctcctg t                                            21

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 26
gcccaatacg accaaatccg                                              20

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 27
cctccggagt aactcagtgc                                              20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
acaacttacc gagcgaaagc                                              20
```

```
<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 29
gcacactgaa gtggcacagt                                               20
```